(12) United States Patent
Boldenow et al.

(10) Patent No.: US 8,021,351 B2
(45) Date of Patent: Sep. 20, 2011

(54) TRACKING ASPIRATION CATHETER

(75) Inventors: Gregory A. Boldenow, St. Michael, MN (US); Jason A. Galdonik, Hanover, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 749 days.

(21) Appl. No.: 11/207,169

(22) Filed: Aug. 18, 2005

(65) Prior Publication Data

US 2007/0060944 A1    Mar. 15, 2007

(51) Int. Cl.
A61M 25/00 (2006.01)
(52) U.S. Cl. ....................................... 604/523
(58) Field of Classification Search .................. 604/509, 604/523; 606/200
See application file for complete search history.

(56) References Cited

U.S. PATENT DOCUMENTS

| | | |
|---|---|---|
| 4,610,662 A | 9/1986 | Weikl et al. |
| 4,723,549 A | 2/1988 | Wholey et al. |
| 4,728,319 A | 3/1988 | Masch |
| 4,784,636 A | 11/1988 | Rydell |
| 4,790,812 A | 12/1988 | Hawkins, Jr. et al. |
| 4,794,928 A | 1/1989 | Kletschka |
| 4,873,978 A | 10/1989 | Ginsburg |
| 4,883,460 A | 11/1989 | Zanetti |
| 4,887,613 A | 12/1989 | Farr et al. |
| 4,994,067 A | 2/1991 | Summers |
| 5,011,488 A | 4/1991 | Ginsburg |
| 5,011,490 A | 4/1991 | Fischell et al. |
| 5,053,008 A | 10/1991 | Bajaj |
| 5,059,178 A | 10/1991 | Ya |
| 5,102,415 A | 4/1992 | Guenther et al. |
| 5,108,419 A | 4/1992 | Reger et al. |
| 5,152,277 A | 10/1992 | Honda et al. |
| 5,163,906 A | 11/1992 | Ahmadi |
| 5,211,651 A | 5/1993 | Reger et al. |
| 5,549,626 A | 8/1996 | Miller et al. |
| 5,599,307 A | 2/1997 | Bacher et al. |
| 5,766,191 A | 6/1998 | Trerotola |

(Continued)

FOREIGN PATENT DOCUMENTS

WO    WO 95/05209    2/1995

(Continued)

OTHER PUBLICATIONS

Feldman, "Transcatheter Aspiration of a Thrombus in an Aortocoronary Saphenous Vein Graft," Am. J. Cardiol. Aug. 1, 1987, 60(4), 379-380.

(Continued)

Primary Examiner — Nicholas D Lucchesi
Assistant Examiner — Victoria P Campbell

(57) ABSTRACT

In general, aspiration catheters have a suction device, a proximal portion and a shaft with a proximal end and a distal end. Improvements in the aspiration catheter design provide for improved tracking and/or reduced chance of snagging during delivery of the aspiration catheter. In some embodiments, the tip of the shaft has a curve relative to the neutral orientation of the remaining portions of the shaft. In other embodiments, the aspiration catheter further comprises a tracking portion that has a guide lumen. A guide structure can extend through the guide lumen to limit the motion of the tip of the catheter relative to the guide structure during delivery of the aspiration catheter within a patient's vessel. In further embodiments, the aspiration catheter comprises a deflection structure having a tether and a bumper. Improved methods for using the aspiration catheter to recover an embolism protection device are described.

18 Claims, 11 Drawing Sheets

U.S. PATENT DOCUMENTS

| | | |
|---|---|---|
| 5,814,064 A | 9/1998 | Daniel et al. |
| 5,827,229 A | 10/1998 | Auth et al. |
| 5,836,868 A | 11/1998 | Ressemann et al. |
| 5,843,051 A | 12/1998 | Adams et al. |
| 5,897,567 A | 4/1999 | Ressemann et al. |
| 5,911,725 A | 6/1999 | Boury |
| 5,911,734 A | 6/1999 | Tsugita et al. |
| 5,938,645 A | 8/1999 | Gordon |
| 5,941,869 A | 8/1999 | Patterson et al. |
| 5,997,557 A | 12/1999 | Barbut et al. |
| 6,010,522 A | 1/2000 | Barbut et al. |
| 6,022,336 A | 2/2000 | Zadno-Azizi |
| 6,135,991 A | 10/2000 | Muni et al. |
| 6,142,987 A | 11/2000 | Tsugita |
| 6,159,195 A | 12/2000 | Ha et al. |
| 6,168,579 B1 | 1/2001 | Tsugita |
| 6,203,561 B1 | 3/2001 | Ramee et al. |
| 6,206,868 B1 | 3/2001 | Pairodi |
| 6,270,477 B1 | 8/2001 | Bagaoison et al. |
| 6,361,545 B1 | 3/2002 | Macoviak et al. |
| 6,454,741 B1 | 9/2002 | Muni et al. |
| 6,485,500 B1 | 11/2002 | Kokish |
| 6,569,148 B2 | 5/2003 | Bagaoisan et al. |
| 6,596,011 B2 | 7/2003 | Johnson et al. |
| 6,620,148 B1 | 9/2003 | Tsugita |
| 6,805,692 B2 | 10/2004 | Muni et al. |
| 6,911,036 B2 | 6/2005 | Douk et al. |
| 7,166,120 B2 | 1/2007 | Kusleika |
| 7,229,464 B2 | 6/2007 | Hanson et al. |
| 7,323,002 B2 | 1/2008 | Johnson et al. |
| 2002/0035347 A1 | 3/2002 | Bagaoisan |
| 2002/0169472 A1 | 11/2002 | Douk et al. |
| 2003/0023263 A1 | 1/2003 | Krolik et al. |
| 2003/0135232 A1 | 7/2003 | Douk et al. |
| 2004/0006365 A1 | 1/2004 | Brady et al. |
| 2004/0015151 A1* | 1/2004 | Chambers .................... 604/532 |
| 2004/0059280 A1* | 3/2004 | Makower et al. ................ 604/8 |
| 2004/0116900 A1* | 6/2004 | Silva et al. .................... 604/523 |
| 2004/0254602 A1 | 12/2004 | Lehe et al. |
| 2005/0021075 A1 | 1/2005 | Bonnette et al. |
| 2005/0277976 A1 | 12/2005 | Galdonik et al. |
| 2006/0190024 A1* | 8/2006 | Bei et al. ...................... 606/200 |

FOREIGN PATENT DOCUMENTS

| | | |
|---|---|---|
| WO | WO 98/38930 | 9/1998 |
| WO | WO 02/085092 | 10/2002 |

OTHER PUBLICATIONS

Nakagawa et al., "A Retrievable Nitinol Vena Cava Filter: Experimental and Initial Clinical Results," J. of Vascular and Interventional radiology, May-Jun. 1994; 5:507-512.

* cited by examiner

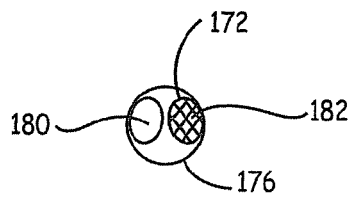
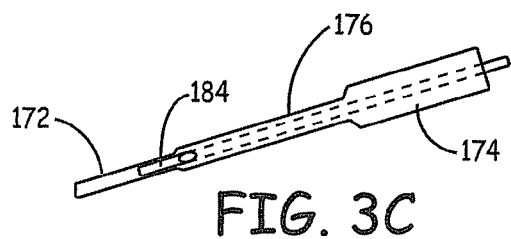
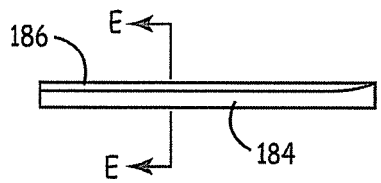
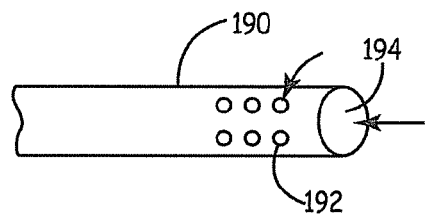
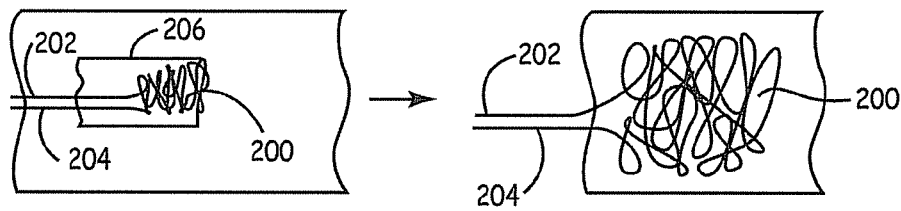
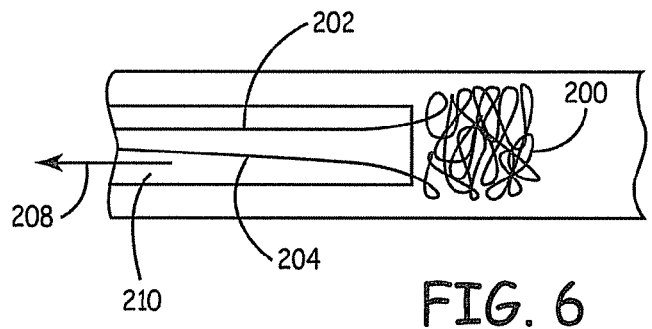

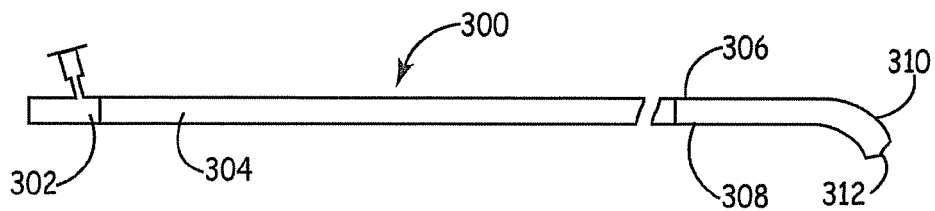
FIG. 11
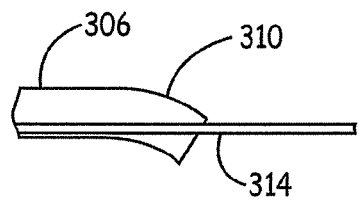
FIG. 12
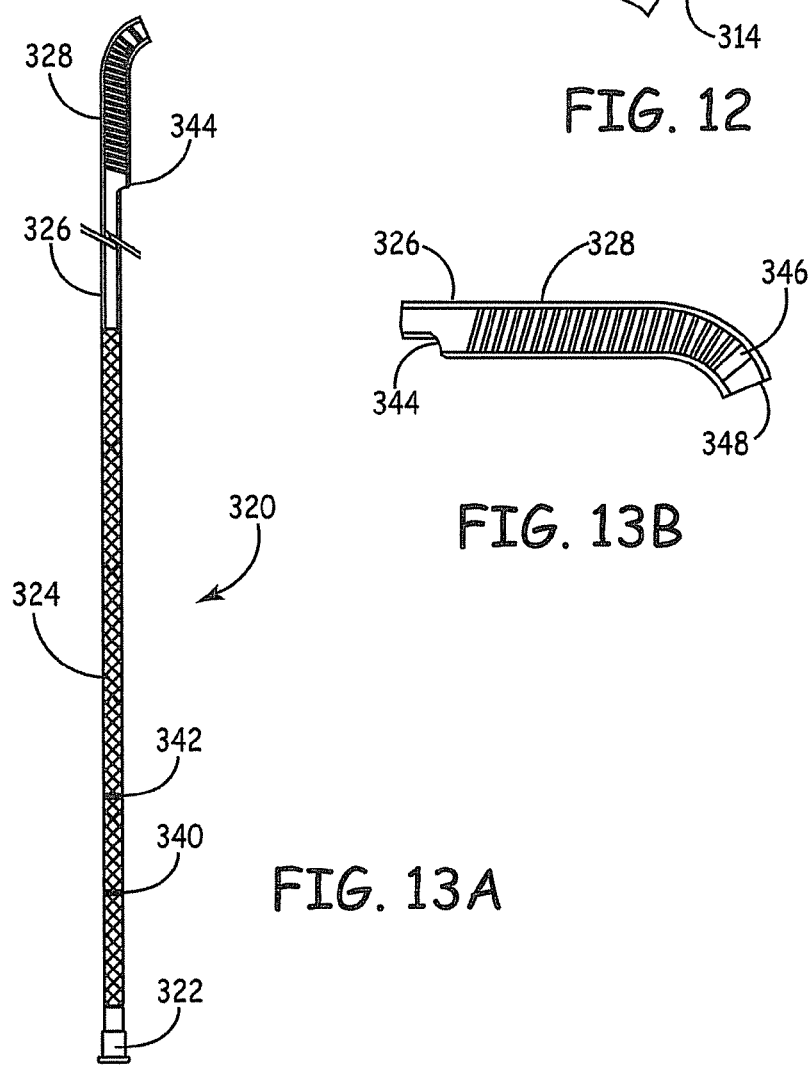
FIG. 13B
FIG. 13A

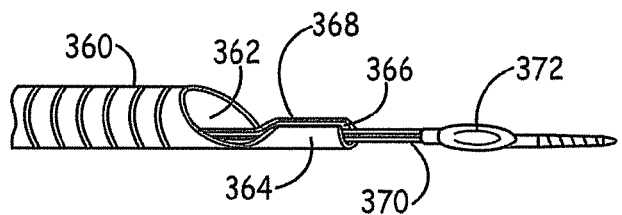
FIG. 15
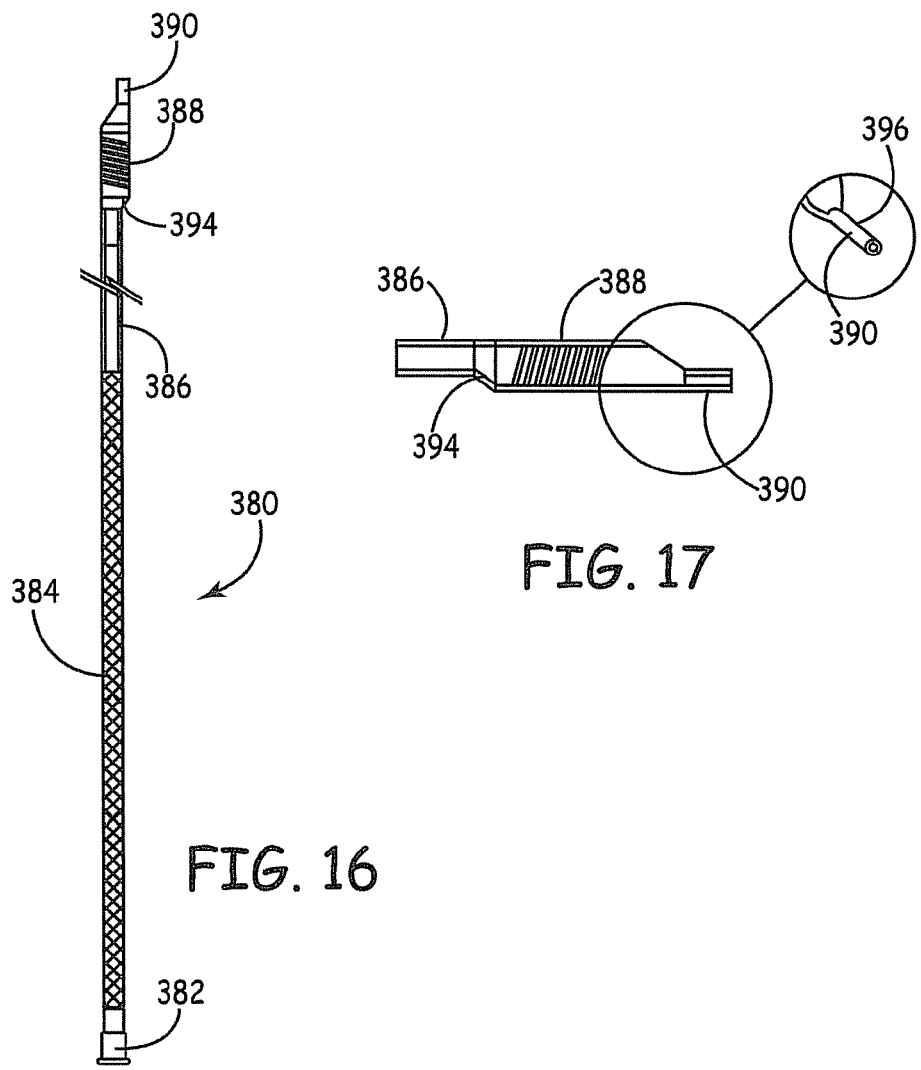
FIG. 17
FIG. 16

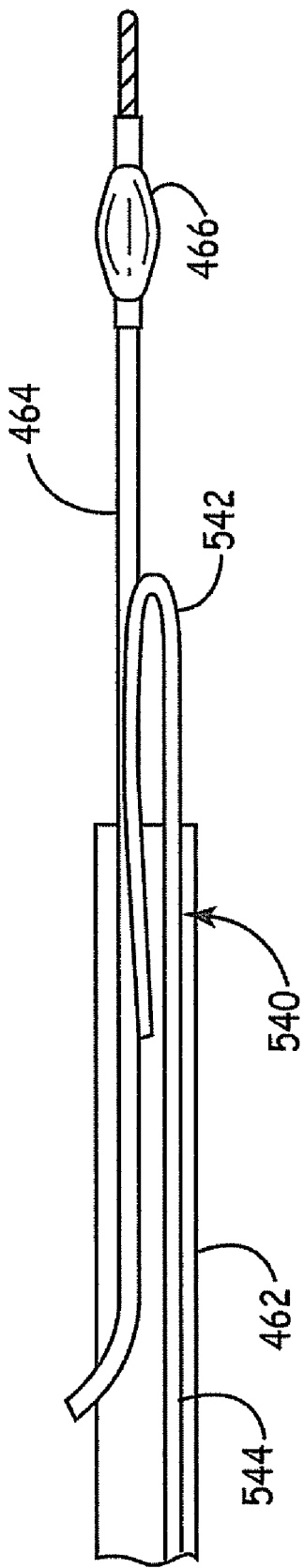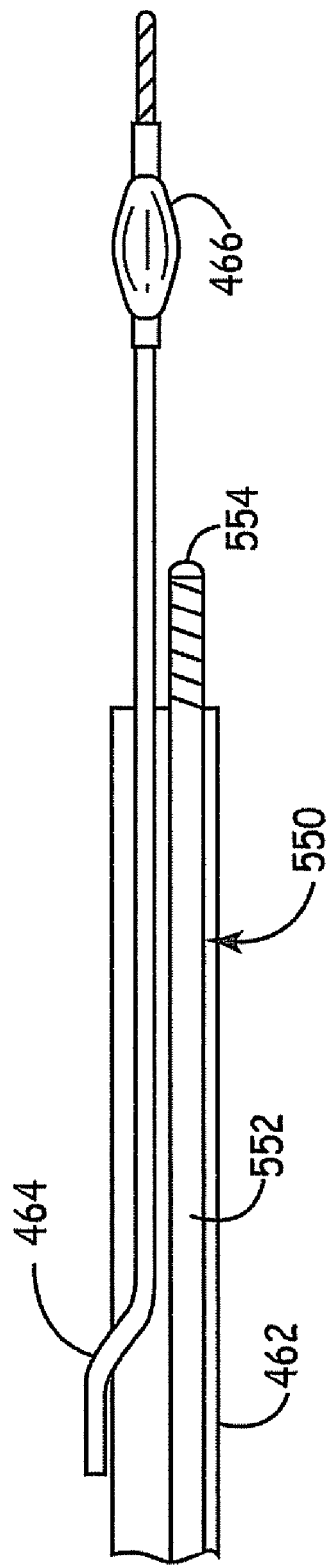

TRACKING ASPIRATION CATHETER

FIELD OF THE INVENTION

The invention relates to aspiration catheters with improved tracking. In some embodiments, the invention relates to catheters for the removal of emboli traps, i.e. embolism protection devices. For some specific embodiments, the invention relates to aspiration catheters that facilitate the removal of an embolism protection device, which can have a three-dimensional filtering matrix, from a patient's vessels with reduced or eliminated release of emboli. The invention further relates to improved method for tracking aspiration catheters.

BACKGROUND OF THE INVENTION

An embolus can be any particle comprising a foreign and/or native material, which enters the vascular system or other vessel of the body with potential to cause occlusion of blood flow. Emboli can be formed from aggregates of fibrin, blood cells or fragments thereof, collagen, cholesterol, plaque, fat, calcified plaque, bubbles, arterial tissue, and/or other miscellaneous fragments or combinations thereof. Emboli can lodge in the narrowing regions of medium size blood vessels that feed the major organs. Loss of blood flow to surrounding tissue causes localized cell death or microinfarcts. Cerebral microinfarcts can cause stroke leading to confusion, disturbance of speech, paralysis, visual disturbances, balance disturbances and even death. In the heart, emboli can cause myocardial infarcts, i.e. heart attacks. Myocardial infarction refers to the death of a section of myocardium or middle layer of the heart muscle. Myocardial infarction can result from at least partial blockage of the coronary artery or its branches. Blockage of capillaries associated with the coronary arteries can result in corresponding microinfarctions/microinfarcs. Resulting impairments are frequently short term but can be permanent.

Disease states including arteriosclerosis and deep vein thrombosis, aging and even pregnancy can cause build up of plaque and fibrin on vessel walls. Anything that loosens or breaks up this plaque can generate emboli. The clinical ramifications of emboli are staggering. Emboli generated from arteriosclerosis of the carotid artery alone cause 25% of the 500,000 strokes that occur yearly in the United States (2002 American Heart Association And Stroke annual statistics).

Many clinical procedures can result in emboli including, for example, coronary, carotid, and peripheral interventions. In these cases, particulate matter, including, for example, plaque, debris and thrombus, can form emboli distal to the site of intervention. As a result, blood flow to the distal vascular bed can be diminished and periprocedural end-organ ischemia and infarction can result. Distal embolization of large particles produced at the time of such interventions as balloon inflation or stent deployment may obstruct large, epicardial vessels, and smaller particles (as small as 15-100 microns) can cause microinfarcts and/or myocardial infarctions and left ventricular dysfunction.

Each year there are approximately 800,000 cardiac surgical cases, which involve cardiopulmonary bypass (CPB) worldwide. Of these cardiac surgical cases, approximately 48,000 suffer stroke and nearly 300,000 experience some neurocognitive disturbance. This is a significant clinical problem. These complications are due in large measure to CPB-generated emboli. The average number of emboli measured by Trans Cranial Doppler (TCD) in patients undergoing cardiopulmonary bypass is 183 (range 3-947). The majority of emboli end up in the very distal cerebral tree, the terminal arterioles and capillaries causing microinfarctions, (i.e., loss of blood to surrounding tissue).

Ironically, the surgical interventions used to remove or bypass the plaque of arteriosclerosis (e.g., balloon dilatation angioplasty, endarterectomy, bypass grafting and stenting) can themselves disrupt plaque. One of the most common cardiovascular interventions is coronary artery bypass grafting (CABG). Historically, 10-20% of all CABG interventions generate emboli large enough to cause myocardial infarcts. This is particularly true when the graft used is of saphenous vein origin. But CABG is not the only procedure with potential to generate emboli. In fact, doppler ultrasound shows evidence of microembolization in almost all cardiac intervention cases. Of the over 1.8 million intervention procedures performed annually, greater than 10% result in neurocognitive disturbance and/or ischemic event. These impairments are frequently short term, but can be permanent.

Ten percent is currently considered an acceptable complication rate, however as the number of procedures continues to grow (15-35% increase annually depending on specific procedure (Medical And Healthcare Marketplace Guide, 17th Edition Volume 1, Research Reports 2001-2002, incorporated herein by reference.) the total number of patients affected grows. As this number increases so does patient care spending. While daunting, cost figures fail to include the social and financial burden placed on family members upon hospital release. In summary, embolic events complicating percutanuous endovascular procedures cause high rates of clinically observed neurological disturbances and cardiovascular disease, decreased quality of life and increased patient care spending. Thus, there is a significant clinical need for effective prevention of adverse embolic events.

A significant reason for ischemic injury during percutaneous procedures can be generation of emboli which block smaller distal vessels. One approach to curb this complication has been to use pharmacological therapies during the time of the intervention. Limited therapeutic success has been reported with the use of calcium channel blockers, adenosine, and sodium nitroprusside (Webb, J G, Carere, R G, Virmani, R, Baim, D, Teirstein, P S, Whitlow, P, McQueen, C, Kolodgie, F D, Buller, E, Dodek, A, Mancini, G B, & Oesterle, S: Retrieval and analysis of particulate debris after saphenous vein graft intervention. *J Am Coll Cardiol* 2000, 34:468-475, incorporation herein by reference). Glyoprotein IIb/IIIa inhibitors have been used for percutaneous coronary interventions to reduce platelet aggregation, but also fail to show meaningful long term clinical benefit. (Mathew, V, Grill, D E, Scott, C G, Grantham, J A, Ting, H H, Garratt, K N, & Holmes, D R, Jr. The influence of abciximab use on clinical outcome after aortocoronary vein graft interventions. *J Am Coll Cardiol* 1999, 34:1163-1169 and Mak, K H, Challapalli, R, Eisenberg, M J, Anderson, K M, Califf, R M, & Topol, E J: Effect of platelet glycoprotein IIb/IIIa receptor inhibition on distal embolization during percutaneous revascularization of aortocoronary saphenous vein grafts. EPIC Investigators. Evaluation of IIb/IIIa platelet receptor antagonist 7E3 in Preventing Ischemic Complications. *Am J Cardiol* 1997, 80:985-988, both of which are incorporated herein by reference.) Since embolization often develops from physical disruption of fibrotic plaque, a mechanism of therapeutic embolic protection specifically targeted at prevention of platelet aggregation and blood clotting may have little effect on these already-formed, embolizable plaques.

Surgical procedures for the treatment of renal artery stenosis can also generate emboli. There is clinical evidence to suggest that 36% of those treated suffer arteriolar nephrosclerosis caused by atheroemboli. Five-year survival of patients with atheroembolic events is significantly worse than of patients without atheroemboli (54% vs. 85% respectively) [Krishmamurthi et al. J. Urol. 1999, 161:1093-6].

Foreign material in the stream of flow can cause turbulence or low flow. Such flow conditions have been shown to increase rates of infection. Thrombus not only generates emboli, but also increases the risk of infection. It is evident that a wide variety of embolic events cause high rates of clinically observed symptoms, decreased quality of life and increased patient care spending.

SUMMARY OF THE INVENTION

In a first aspect, the invention pertains to an aspiration catheter comprising a suction device, a proximal portion and a shaft with a proximal end and a distal end. The shaft is operably connected at its proximal end to the proximal portion to form a suction lumen. The suction device is attached or attachable to the proximal portion to operably connect the suction device to the suction lumen. In addition, the shaft comprises a tip at the distal end of the shaft having an aspiration opening. The tip has a natural curve relative to the natural orientation of the shaft.

In another aspect, the invention pertains to an aspiration catheter comprising a suction device, a proximal portion, a shaft and a tracking portion. The shaft comprises an aspiration lumen having a distal opening, and the suction device is attached or attachable to the proximal portion to form a continuous lumen extending from the suction device to the distal opening. The tracking portion presents a guide lumen at or near to the distal opening. The guide lumen has a diameter significantly less than the aspiration lumen. Also, the tracking portion is configured not to block significantly the distal opening or has a shifted aspiration configuration in which the distal opening is not blocked significantly.

In a further aspect, the invention pertains to an aspiration catheter comprising a suction device, a proximal portion, a shaft and a deflection structure. The shaft comprises an aspiration lumen having a distal opening, and the suction device is attached or attachable to the proximal portion to form a continuous lumen extending from the suction device to the distal opening. Furthermore, the deflection structure comprises a bumper and a tether and has a first configuration wherein the bumper extends out from the distal opening.

Furthermore, the invention pertains to a method for the removal of an embolism protection device from a patient's vessel. The method comprises applying suction while an aspiration catheter is being moved in a distal direction along a guide structure toward the embolism protection device in a deployed configuration. The method further comprises collapsing an embolism protection device in a retrieval configuration within the aspiration catheter while applying suction through the aspiration catheter.

In addition, the invention pertains to a method for the delivery of an aspiration catheter with a suction port at its distal end. The method comprises delivering the aspiration catheter over a guide structure within a patient's vessel. The guide structure extends from the suction port but is constrained relative to the suction port so that the guide structure cannot move freely over the suction opening. The method further comprises disengaging the guide structure so that it is not constrained relative to the suction opening.

In other aspects, the invention pertains to a method for the delivery of an aspiration catheter with a suction port at its distal end. The method comprises delivering the aspiration catheter over a guide structure with a bumper extending from the suction port; and withdrawing the bumper away from the suction port.

Additionally, the invention pertains to a method for the delivery of an aspiration catheter with a distal suction port. The method comprises tracking a catheter along a guide structure with close tracking resulting from a curve in the catheter tip. Also, the catheter comprises a metal braid within a polymer to increase torque transmittal along the length of the catheter.

BRIEF DESCRIPTION OF THE DRAWINGS

FIG. 3B is a sectional view of an embodiment of the aspiration catheter of FIG. 3A having a screen between a rapid exchange segment and a shaft.

FIG. 3C is a fragmentary side view of an embodiment of the aspiration catheter of FIG. 3A having a tube within a port for directing a guidewire through the port.

FIG. 3D is a side view of a particular embodiment of a loading tool.

FIG. 3E is a sectional view of the loading tool of FIG. 3D taken along line E-E of FIG. 3D.

FIG. 4 is a fragmentary side view of an aspiration catheter with side passages near the distal end of the catheter.

FIG. 5 is a schematic side view of an embodiment of an embolism protection device with a tether to facilitate removal within a patient's vessel with the left view showing the deployment of the device from a deployment apparatus and the right view showing the device following deployment.

FIG. 6 is a schematic side view showing the use of the tether to remove the device of FIG. 5.

FIG. 11 is a side view of a rapid exchange aspiration catheter with a curved tip.

FIG. 12 is a fragmentary view of the curved tip of the aspiration catheter of FIG. 11 interfacing with a guide structure.

FIG. 13A is a side view of a specific embodiment of a rapid exchange aspiration catheter with a curved tip.

FIG. 13B is an expanded fragmentary view of the curved tip of the aspiration catheter of FIG. 13A.

FIG. 15 is a fragmentary view of an aspiration catheter having an extension at its tip with a guide lumen shown with a guide structure extending from the aspiration lumen of the catheter through the guide lumen of the extension.

FIG. 16 is a side view of a specific embodiment of an aspiration catheter having an extension at its tip with a guide lumen.

FIG. 17 is an expanded side view of the rapid exchange segment of the aspiration catheter of FIG. 16.

FIG. 35 is a fragmentary side view of an aspiration catheter having a fifth embodiment of a deflection structure having a bumper.

FIG. 36 is a fragmentary side view of an aspiration catheter having a sixth embodiment of a deflection structure having a bumper.

DETAILED DESCRIPTION OF THE INVENTION

Figure 1:
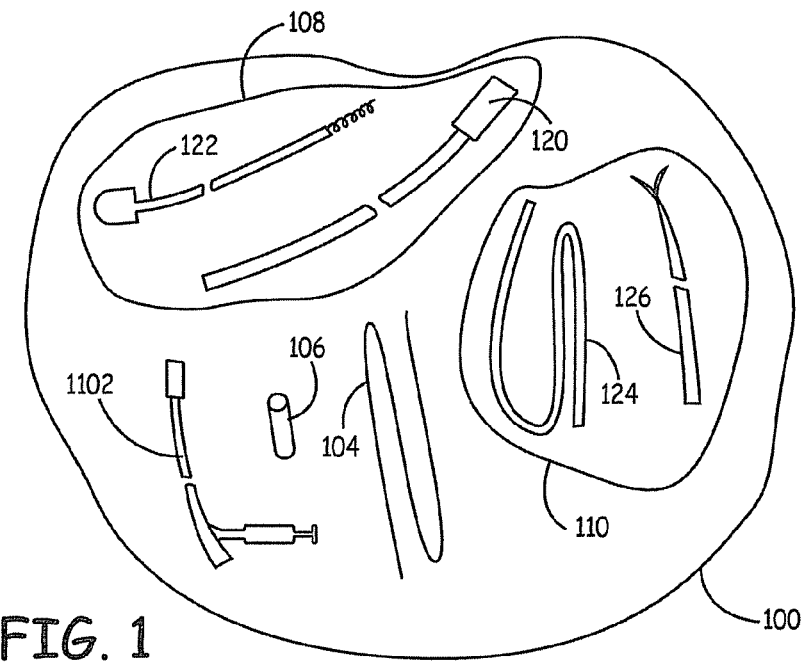
FIG. 1 is a schematic representation of a system for the delivery and use of an aspiration catheter.

Improved aspiration catheters provide significantly better tracking during delivery into a patient's vessel. In some embodiments, the improved aspiration catheters have a curved tip that controls tracking along a guide structure extending from the tip. In further embodiments, the improved catheter has a constricted guide lumen at or near the distal end of the catheter that controls the tracking of the catheter tip. In additional embodiments, the improved catheter designs have a protrusion extending as a bumper from the distal end of the catheter tip such that snagging of the catheter tip can be reduced or eliminated. These features of the catheter can be combined within specific structures. The improved embodiments of an aspiration catheter generally can have a rapid exchange structure or an over-the-wire structure. Additionally or alternatively, it can be advantageous to form the very distal portion of the catheter tip from a very flexible material. These aspiration catheter structures can be especially advantageous for the retrieval of an embolism protection device, such as an embolism protection device with a three-dimensional filtration matrix. The design of the aspiration catheter can provide for withdrawal of an embolism protections device into the catheter for retrieval of the embolism protection device while providing improved tracking during delivery.

In general, aspiration can be applied within a patient's vessel to collect debris or otherwise facilitate performance of other procedures within the vessel. The aspiration catheters, corresponding treatment systems and corresponding procedures described herein are generally used on mammalian patients, in particular humans, farm animals or pets. Similarly, these procedures and devices can be used in a blood vessel, e.g., an artery or a vein, urinary tract vessel, reproductive tract vessel or other vessel of the patient.

In general, the aspiration catheters can be used in any appropriate medical procedure within a patient. For example, the aspiration catheters can be used to apply suction to the inside surface of a stent following delivery of the stent in the patient to remove any debris created during the procedure along the inside surface of the stent. Also, the aspiration catheters can be used generally for the removal of debris in a thrombectomy procedure. However, in embodiments of particular interest, the aspiration catheter can be used to facilitate the retrieval of an embolic protection device from the patient's vessel.

Embolic protection devices generally filter fluid flowing within the vessel to capture emboli within the flow. Embolism protection devices can be delivered in response to a variety of circumstances. For example, the device can be delivered prior to performance of a medical procedure that has the potential of resulting in the release of emboli. Similarly, one or more devices can be implanted following an injury or trauma that can result in the formation and/or release of emboli. In addition, one or more devices can be implanted in an individual that had developed a physiological condition in which emboli may develop. The devices can be used in conjunction with other therapeutic device(s) and/or therapy such as drug therapy. Embolism protection devices of particular interest have three dimensional filtering matrices, as described further below, although other devices may substantially or completely block flow, such as a balloon based embolism protection device.

Filtering devices can collect some or all emboli of concern from a particular flow. Regardless of the circumstances in which the device is implanted, many embodiments subsequently have indications calling for the subsequent removal, i.e., recovery, of the device. In particular, in most cases, the embolism protection device is removed from the flow generally after the causes of an embolic event are no longer present. The removal of the device from the patient can disrupt the device in a way that can result in release of some of the emboli from the device. Any released emboli can flow down stream and pose a risk to the patient.

Recovery can be performed, for example, after conclusion of a specific medical procedure, after a particular risk has passed or in conjunction with the placement of another replacement embolism protection device. Manipulating the embolism protection device can create a risk associated with dislodging emboli entrapped in the device and release of the emboli into the patient's fluid flow, whether blood or other fluid. The devices and procedures described herein facilitate the removal of an embolism protection device with reduced or eliminated loss of trapped emboli during the removal of the device. The devices and procedures can be used with respect to embolism protection devices that are not attached after delivery or embolism protection devices that remain attached after delivery.

In general, the aspiration catheters can be used for the retrieval of a range of embolism protection devices. However, embolism protection devices of particular interest comprise a three-dimensional filtering matrix. Furthermore, while embolism protection devices can be left within a vessel untethered for a period of time for later removal, in embodiments of particular interest the embolism protection device is formed as an integral component of an integrated guiding structure for tethered placement within a vessel during a procedure and subsequent removal. The three-dimensional filtration matrix of the embolism protection devices provide for improved emboli capture with reduced or eliminated restriction of natural flow during deployment, and the aspiration catheters described herein provide for improved retrieval of the embolism protection devices with reduced or eliminated risk of releasing emboli downstream during the recovery process.

Aspiration systems generally comprise a guide structure, an aspiration catheter, an optional embolism protection device and optional additional treatment structures. In some embodiments, one or more of these components of the system can be integrated together. Suitable additional treatment structure can be, for example, an angioplasty balloon, a stent deployment tool, an embolectomy device or any other suitable treatment device that can be delivered into a patient's vessel. In some embodiments, these additional treatment structures can be used and removed prior to use of the aspiration catheter.

For embodiments in which an embolism protection device is left un-tethered within the patient and subsequently retrieved, the system generally comprises a delivery tool and a recovery tool for the respective delivery and recovery of the device. The aspiration catheters described herein can be used with these embodiments with un-tethered embolism protection devices. Specifically, the aspiration catheter can be used, for example, in conjunction with the recovery tool. The use of aspiration catheters generally for the recovery of un-tethered embolism protection devices is described further in copending U.S. patent application Ser. No. 10/854,920 to Galdonik et al., entitled "Emboli Filter Export System," incorporated herein by reference.

The integrated guide structure can be a guidewire or an integrated guiding device. An integrated guiding device comprises a thin corewire and a small diameter tubing/catheter, e.g., a hypotube or polytube, that goes over the corewire generally with a torque coupler to couple the small diameter tubing to the corewire. A torque coupler can provide considerable advantages with respect to delivery of the integrated guiding device while providing for desired longitudinal relative motion of the corewire and tube. The integrated guiding device can be used for the delivery of appropriate medical treatment devices and the like. A specific embodiment of an integrated guide device is described below with respect to an associated fiber-based embolic protection device. Integrated guide structures and torque couplers are described further in copending U.S. application Ser. No. 11/072,001 to Galdonik et al., entitled Steerable Device Having A Corewire Within A Tube And Combination With A Functional Medical Component," incorporated herein by reference.

In general, the aspiration catheter has a suction device, a proximal section where the suction device connects to a suction lumen, a shaft, with a suction lumen extending from the suction device through the shaft to a distal suction opening. Generally, the aspiration catheter comprises a radiopaque marker at or near its distal end. The distal end of the shaft can have a rapid exchange segment and/or an enlarged compartment to facilitate withdrawal of an embolism protection device within the tip of the catheter. Generally, the aspiration catheter tracks along the guide structure during delivery into a patient. Improved structures described herein have improved tracking with respect to ease of maneuvering bends and branches in the vessel as well as a reduced chance of snagging, for example, on medical devices such as a stent within the vessel or on natural structures within the vessel.

Embolic protection devices generally restrict passage of emboli downstream from the device. In some embodiments, the embolism protection device is a filter that removes emboli from flow that continues through the filter. In embodiments of particular interest, the embolism protection device has a three-dimensional filtering matrix that has a plurality of interconnected flow passages through the filter. These three dimensional filtering matrices provided improved filtration while having little if any pressure drop across the filter matrix. A fiber-based embolism protection component connected to an integrated guiding device is described further below. In this device, the fibers are attached at one end to the corewire and at the other end to the tube, e.g., a hypotube. The device can be deployed with the fibers stretched into a relatively low profile configuration. Upon longitudinal pulling the corewire proximal relative to the tube, the fibers flare outward to a deployed configuration in which the device can provide filtering within a patient's vessel. Reversal of the longitudinal motion of the corewire relative to the tube can stretch the fibers to a removal configuration. Additional embodiments of embolism protection devices are described in copending U.S. patent application Ser. No. 10/414,909 to Ogle, entitled "Embolism Protection Device," incorporated herein by reference. Aspiration can be applied during the removal of the device, as described further in copending U.S. patent application Ser. No. 10/854,920 filed May 27, 2004 to Galdonik et al., entitled "Emboli Filter Export System," incorporated herein by reference.

In some embodiments, the fiber-based embolism protection device comprises surface capillary fibers. Experiments indicate that devices formed with surface capillary fibers provide excellent filtering properties. Embolism protection devices with surface capillary fibers are described further in copending U.S. patent application Ser. No. 10/795,131 filed Mar. 6, 2004 to Galdonik et al., entitled "Fiber Based Embolism Protection Device," incorporated herein by reference. It has been discovered that the twisting of a fiber bundle, such as an SCF fiber bundle, in an embolism protection device can assist with keeping the fibers free of gaps during deployment and can result more consistent performance of the filter following deployment in a patient. Rotationally locking the tube to the corewire allow for the fiber bundle to be twisted and for the twist to be preserved through sterilization and final use of the device. In some embodiments, gentle heat can be added during the manufacturing process to impart a shape memory into the polymer, although heat is not required for consistent performance of the device or for elimination of gaps in the deployed fibers. In further additional or alternative embodiments, the fiber bundle can be twisted while the fibers are being deployed.

The general structure of an aspiration catheter is described above. The improved designs described herein can have improved tracking along a guide structure and a reduced likelihood of snagging within the vessel. In some embodiments, the catheter tip has a curved configuration, optionally with a beveled edge. In these embodiments, the guide structure deflects the bent tip such that the guide structure at least partially guards the opening of the aspiration catheter during the delivery of the guide catheter through the patient's vessel. Also, the curved tip facilitates tracking of the catheter along the guide structure with a reduced tendency of the catheter to redirect the guide structure at branches or curves in the vessel.

In other embodiments, the aspiration catheter has a tracking guide at or near the distal end of the catheter. The tracking guide constrains the movement of the aspiration catheter opening relative to the guide structure projecting from the opening by providing a narrow guide lumen through which the guide structure passes. Due to the guide lumen, the aspiration catheter closely follows the path of the guide structure without a tendency to move the guide structure at bends or branches in the vessel. The narrow lumen can be provided, for example, with a structure extending from the tip of the catheter or with a lumen through a guide component extending within the aspiration opening, which can further shield the aspiration opening from snagging. To provide for retrieval of an embolism protection device into the tip of the aspiration catheter, the guide component at the catheter tip may be drawn into the aspiration catheter with a tether or the like, or a guide structure may be released from the guide component of the catheter.

Additionally or alternatively, the aspiration catheter can comprise a deflection structure with a bumper that extends from the aspiration opening that at least partially shields the aspiration opening during delivery of the aspiration catheter. The bumper can be an extension from a tether, shaft or the like. In some embodiments, the bumper can be withdrawn partially or completely to apply aspiration and/or to draw an embolism protection within the aspiration catheter.

In general, the particular procedure for the use of the aspiration catheter depends on the specific application. In general, the aspiration catheter is directed along a guide structure that has already been placed in the patient. An introducer catheter can be used to form a non-disruptive lumen through larger vessel for introduction of the aspiration catheter and/or other medical devices, such as those to be introduced over the guide structure. Aspiration can be applied in general once the aspiration catheter has exited from the introducer catheter, although in some embodiments, aspiration is not applied while the aspiration catheter is moving or not applied until the aspiration catheter is at or near a target location within the vessel.

For retrieval of an embolism protection device, the aspiration catheter generally is positioned relatively close to the deployed device. In some embodiments, a guide component of the catheter is transitioned to a retrieval position such that the embolism protection device can enter into the opening of the aspiration catheter. This transition can be performed prior to the beginning as aspiration, although it can also be performed while aspiration is being applied or at a break in application of aspiration. Some designs of guide lumens disengage automatically as the embolism protection device is brought near the aspiration opening of the aspiration catheter.

In general, for any of the various embodiments, at some point in time, it may be desirable to remove the embolism protection device from the patient. In order to avoid negating at least some of the beneficial effects of the embolism protection device, it is desirable to avoid release of emboli during the recovery of the embolism protection device. Suction alone or combined with covering the embolism protection device in a sheath can be used to reduce or eliminate release of emboli from the embolism protection device during recovery.

Generally, suction can be applied as the embolism protection device is transformed from a deployed configuration to a configuration with a narrower profile for withdrawal. The embolism protection device can be transformed from the deployed configuration with an actuator, such as a hypotube—corewire integrated system, that directly converts the device from the deployed configuration to a recovery configuration. Alternatively or additionally, the embolism protection device can be mechanically compressed into a recovery configuration. In the recovery configuration, the device does not extend across the cross section of the vessel lumen such that it can be withdrawn from the vessel, generally along a guidewire and/or catheter.

In some embodiments, a sheath is used as a protective lumen for the embolism protection device in the recovery configuration. The sheath for removal of the embolism protection device generally can be provided as a compartment at the distal end of an aspiration catheter. Once the embolism protection device is compacted into its recovery configuration and drawn into the aspiration catheter lumen, the embolism protection device and aspiration catheter can be withdrawn from the patient's vessel. Suction can be applied a short period of time prior to compacting the embolism protection device, during compaction of the embolism protection device, while drawing the embolism protection device into the aspiration catheter, and/or for selected portions of any or all of the steps in the removal process for the embolism protection device.

Improved designs of aspiration catheters described herein provide for improved recovery of an embolism protection device by combining aspiration withdrawal of the device into a sheath for removal. When combined with the selection of appropriately effective embolism protection devices, the systems and procedures herein can effectively filter emboli without restricting flow through the vessel and can provide for removal of the device without significant release of emboli into the flow. Throughout this procedure, the deployment, use and removal of the embolism protection device only results in obstruction of the flow for a brief period in which suction is applied during withdrawal of the embolism protection device into the sheath. Thus, an efficient, easy to use and effective approach is provided for providing embolism protection and restoring the patient to a pre-procedure condition. The improved aspiration catheter embodiments described herein provide for greater ease of delivery and more consistent performance.

Aspiration Catheters and Associated Systems

In general, an aspiration catheter system can comprise an aspiration catheter, a guide structure, an optional embolism protection device, additional optional treatment structures and optional additional procedural structures. Some of these devices can have elements in common with each other. The basic features of an aspiration catheter are described in the following discussion. Aspiration catheter features that provide improved tracking are described in detail in the following section. The guide structure can be a guidewire, an integrated guide device or the like. The guide structure can be used to deliver the aspiration catheter to a desired location within the patient. Embolism protection devices can be recovered with the assistance of an aspiration catheter. In general, an embolism protection device may or may not be tethered when deployed in the patient. Additional procedural structures can be used, for example, to deploy and/or recover the embolism protection device. Additional treatment structures can be, for example, suitable medical devices for the performance of procedures within the vessel, which may or may not involve removal of debris from the vessel. The additional treatment structures may or may not be delivered along the guide structure used for the delivery of the aspiration catheter.

An aspiration catheter system 100 is shown schematically in FIG. 1. In some embodiments, aspiration catheter system 100 comprises an aspiration catheter 102, a guide structure 104, an optional embolism protection device 106, optional treatment structures 108, and optional procedural structures 110. In some embodiments, guide structure 104 can be a conventional guidewire. Various commercial gudewires are available, such as Hi-Torque Spatacore™ guidewire with a stainless steel shaft with a 0.014 inch outer diameter, a flexible tip design and a low friction coating, available from Guidant, Indianapolis, Ind. Below, an integrated guide device, as an alternative to a conventional guidewire, is described as a specific embodiment.

Suitable treatment structures 108 can be, for example, any suitable treatment device suitable for percutaneous delivery to treat a blockage of patient's vessel, an aneurysm or other condition in a vessel. Suitable treatment structures include, for example, angioplasty balloons 120, stents, thrombectomy tools for mechanically disrupting plaque 122, and the like. Suitable angioplasty balloons are described further, for example in U.S. Pat. No. 6,132,824 to Hamlin, entitled "Multilayer Catheter Balloon," incorporated herein by reference. Stent delivery is described further, for example, in U.S. Pat. No. 6,610,069 to Euteneuer et al., entitled "Catheter Support For Stent Delivery," incorporated herein by reference. Various stents and angioplasty balloons are commercially available.

In general, procedural structures 110 can include, for example, catheters 124, cannulas, tools to facilitate delivery and/or recovery of embolism protection devices 126 and the like. In some embodiments in which the embolism protection device is left un-tethered within the patient, the embolism protection device can be deployed with a syringe, catheter, grippers, sheaths, an additional guide structure, a combination thereof or other convenient approach. A delivery tool can interface with a guidewire to guide the embolism protection device to the delivery location. The embolism protection device can be placed within a cannula to enclose the device for delivery. Similar tools can be used to facilitate recovery of an embolism protection device. In addition, a recovery tool can comprise a gripping element that grips the device to reduce its dimensions by physical force such that the embolism protection device can be removed through a catheter or the like. Similarly, the device can be twisted in a cork-screw type fashion to decrease the diameter of the device due to the torque and the compressible nature of the polymers.

For embodiments in which an embolism protection device remains attached after delivery, the delivery tool can comprise one or more tubes, sheaths, rigid extensions, wires, strings, filaments, tethers or the like appropriately positioned for releasing the device. A tether or other attachment structure remains connected between a component outside from the patient and the embolism protection device itself. This attachment structure can comprise a guidewire, an integrated guiding device, a hypotube, a catheter, or the like or combination of similar structures. In some embodiments, strings are placed such that pulling on the string tends to contract the device to reduce or eliminate friction on the vessel wall. For example, the strings can be positioned at or near the outer edge of the device that contacts the vessel wall such that pulling on the string tends to pull the exterior of the device toward the center of the vessel. Tethers and the like also can be useful to maintain an embolism protection device at a delivered position within a vessel.

If the embolism protection device remains attached, the recovery components do not need to comprise a guidewire since some component remains tethered to the embolism protection device throughout the procedure, and the tether can be used for guiding any subsequent structures. In some attached embodiments, a guidewire or corewire remains attached to the embolism protection device throughout the procedure, so that the same guidewire or corewire is available for delivery and recovery of the device. Delivery and recovery tools for tethered and un-tethered devices are described further in copending U.S. patent application Ser. Nos. 10/414,909 to Ogle, entitled "Embolism Protection Device," 10/795,131 to Ogle et al., entitled "Fiber Based Embolism Protection Device," and 10/854,920 to Galdonik et al., entitled "Emboli Filter Export System," all three of which are incorporated herein by reference.

Figure 2:
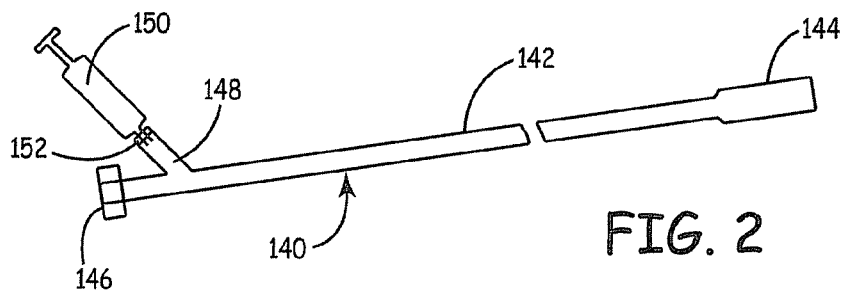
FIG. 2 is a side view of an aspiration catheter with an over the wire design.

While improved features of aspiration catheters especially relating to tracking are described in the following section, some general features of aspiration catheters are described next. Aspiration catheter 102 can comprise an over the wire design or a rapid exchange design. In some embodiments, the aspiration catheter has a compartment at its distal end for withdrawing the embolism protection device from the flow after the filter is retracted from a deployed position. Referring to FIG. 2, aspiration catheter 140 comprises a shaft 142, an optional distal compartment 144, a proximal end 146, an aspiration connection 148 and a suction device 150. Shaft 142 can have an approximately constant diameter, a varying diameter and/or sections with different diameters. In some embodiments, the average outer diameter of shaft 142 ranges from about 0.010 inches to about 0.065 inches and in additional embodiment from about 0.030 inches to about 0.055 inches. For intervention into blood vessels, shaft 142 generally has a length of at least 20 cm, and in some embodiments from about 50 cm to about 300 cm, and in further embodiments from about 100 cm to about 225 cm. Distal compartment 144 generally has a larger diameter compared with the adjacent section of shaft. In particular, in some embodiments, distal compartment 144 has a diameter from about 110 percent to about 200 percent and in further embodiments from about 120 percent to about 175 percent of the average diameter of the ten centimeters of the shaft adjacent distal compartment 144. Distal compartment 144 can have a length from about 0.2 centimeters (cm) to about 3 cm and in further embodiments from about 0.5 cm to about 2 cm. A person of ordinary skill in the art will recognize that additional ranges of sizes are contemplated and are within the present disclosure. The distal compartment or a portion thereof or a position near the distal end of the shaft can comprise a radiopaque marker to provide for visualization using an imaging technique, such as x-ray imaging, for positioning the catheter within the patient.

Proximal end 146 can comprise a handle, ports or other convenient control structures for manipulating aspiration catheter 140 and or the interface of aspiration catheter 140 and other intervention devices. In some embodiments, an aspiration connection 148 can provide for connection of a suction device 150 with a lumen extending through shaft 142. Aspiration connection 148 can be placed at the proximal end or other location near the proximal end, as convenient. Generally, aspiration connection 148 comprises a fitting 152 or the like to provide a sealed connection with suction device 150. Suitable fittings include, for example, conventional fitting, such as an elastomeric diaphragm through which a syringe needle can be inserted or a Luer lock. In other embodiments, the suction device can be formed as an integral part of proximal end 146 such that no fitting or other connection is used. Suitable suction devices include, any suction device that can deliver a selected amount of suction, such as a syringe, a compressed bladder, a pump, such as a peristaltic pump or a piston pump, or the like. A tube or the like can be used to connect the suction device to aspiration connection 148.

Figure 3A:
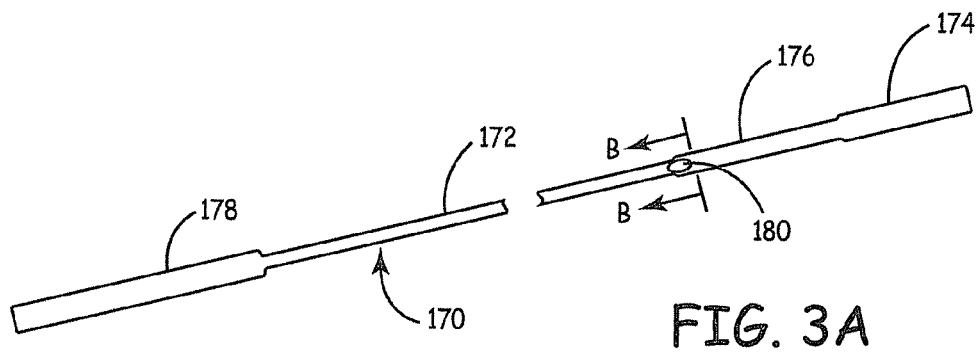
FIG. 3A is a side view of an aspiration catheter with a rapid exchange design.

An embodiment of a rapid exchange aspiration catheter is shown in FIG. 3A. Aspiration catheter 170 has a shaft 172, an optional distal compartment 174, a rapid exchange segment 176, and proximal portion 178. Since shaft 172 does not ride over a guidewire, shaft 172 can have a smaller diameter than shaft 142 of FIG. 1. Distal compartment 174 generally can have similar characteristics as distal compartment 144 of FIG. 1. Proximal portion 178 can provide for the application of suction through an appropriate connection.

In use, rapid exchange segment 176 rides over a guidewire. Therefore, rapid exchange segment 176 generally can have a larger diameter than shaft 172. Guidewire exits through port 180 without blocking suction from shaft 172 that is transmitted to distal compartment 174. To facilitate insertion of the guidewire through port 180, shaft 172 can have a screen 182 at the opening between shaft 172 and rapid exchange segment 176, as shown in FIG. 3B. Screen 182 does not significantly block suction while screen 182 blocks a guide structure from going into the shaft so that it can be directed to the port.

In some embodiments, a tube 184 is inserted through port 180 to guide insertion of a guidewire through port 180, as depicted in FIG. 3C. Specifically, the guidewire can be inserted through the tube through the port, or alternatively into a chamber at the tip and pulled through the port. Then, the tube can be removed for the insertion of the catheter into the patient's vessel. A specific embodiment of a loading tool is shown in FIG. 3D. In this embodiment, loading tool 184 is generally cylindrical with an outer diameter of 0.055 inches and a length of 3.15 inches. A partial circular channel 186 extends along most of the length of the tool. The channel has a depth of approximately 0.012 inches and a radius suitable for holding a standard guidewire with a diameter of 0.014 inches. A sectional view is shown in FIG. 3E. Loading tool 184 abuts adjacent the guide port such that the guide structure is directed to the port rather than the suction lumen. In some embodiments, loading tool does not have a channel but is designed to block the suction lumen such that the guide structure can only enter the guide port.

In some embodiments, rapid exchange segment 176 has a length from about 1 cm to about 35 cm, in further embodiments from about 2 cm to about 30 cm, and in further embodiments from about 5 cm to about 25 cm. The length of the rapid exchange section can be selected to provide desired delivery properties. Rapid exchange segment generally has an outer diameter from about 0.030 inches to about 0.050 inches, and in some embodiments from about 0.035 inches to about 0.045 inches. A person of ordinary skill in the art will recognize that additional ranges of sizes are contemplated and are within the present disclosure. While rapid exchange segment 176 generally tends to be stiffer than shaft 172 due to its greater diameter, the material of the rapid exchange segment can be made more flexible to result in a distal end of the catheter that has better tracking, as described further below.

In some embodiments, the aspiration catheter is designed with specific features to help maintain the suction as the embolism protection device is drawn into the distal end of the aspiration catheter. For example, the distal end can have side ports adjacent the distal end such that a compressed embolism protection device does not block all flow into the catheter. By maintaining the suction, no emboli or fewer emboli are released. Referring to FIG. 4, aspiration catheter 190 has side ports 192. As shown with flow arrows, suction can draw fluid through a distal end port 194 of catheter 190 as well as through side ports 192. Six side ports are shown in FIG. 4. The size, number (such as 1 port, 2-5 ports, or more than 6 ports), and particular positioning can be determined by a person of ordinary skill in the art for a particular design of embolism protection device to obtain appropriate suction.

Embolism protection device 106 can have various sizes and shapes both with respect to the effective exterior surface before and after deployment and with respect to the arrangement of the materials through the cross section of the structure. For example, some membrane based filtration embolism protection devices are commercially available. However, embolism protection devices with a three-dimensional filtering matrix can provide desirable properties for filtering and removal. A three dimensional filtering matrix provides a flow network with multiple flow pathways that flow through the matrix tends not become occluded as smaller emboli are trapped. In some embodiments, embolism protection devices with three-dimensional filtering matrices have an expanding structure that incorporate material, such as hydrogels and/or shape memory fibers. In further embodiments, embolism protection devices incorporate fibers, such as surface capillary fibers, that can be deployed with fibers expanded across the lumen of a patient's vessel to form a three dimensional filtering matrix. Suitable embolism protection devices can be incorporated within an integrated structure for deployment and recovery, with one specific embodiment described below.

An embolus as used herein refers broadly to a particle, besides living cells, in a vessel within a mammal having a diameter of at least about 5 microns. For this determination, the diameter is considered the largest distance between two points on the surface of the particle. Thus, emboli would encompass emboli within the blood as well as kidney stones and the like. Vascular emboli are thought to be composed almost exclusively of clotted blood. Arterial emboli generated in aortic surgery or endovascular intervention can be composed of other components, but it is generally believed that they nearly all contain some component of fibrin. The materials and structure of the device can be selected to have porosity that would allow blood elements, such as white blood cells (about 7-20 microns), red blood cells (8-9 microns) and platelets (2-4 microns), yet collects emboli. In contrast, emboli generally range in size with diameters from about 20 microns to about 3.5 mm, in some embodiments from about 45 microns to about 1000 microns and in further embodiments from about 50 microns to 200 microns. A person of ordinary skill in the art will recognize that additional ranges of emboli within the explicit ranges are contemplated and are within the present disclosure.

Commercially available filtration devices include, for example, the RX Accunet™ Embolic Protection System, available from Guidant, Indianapolis, Ind. This Guidant filter is formed from a nickel-titanium alloy in a mesh. Also, Boston Scientific (Boston, Mass.) markets FilterWire EZ™ Embolic Protection System. The Boston Scientific device has a polyurethane filter. See also, U.S. Pat. No. 6,695,813 to Boyle et al., entitled "Embolic Protection Devices," and U.S. Pat. No. 6,391,045 to Kim et al., entitled "Vena Cava Filter," both of which are incorporated herein by reference.

In some embodiments, an embolism protection device can comprise a polymeric substrate (media, sponge), especially an expandable polymer, such as a swelling polymer, a memory polymer or a compressed polymer. Specifically, in some embodiments, the embolism protection devices described herein generally comprise a swelling polymer that expands, generally spontaneously, upon contact with an aqueous solution, such as blood or other body fluids. Swelling is considered broadly in terms of significant changes in dimension due to absorption or other intake of fluid/liquid into the structure of the material, such as with a sponge, a hydrogel or the like. Hydrogels are generally hydrophilic polymers that are nevertheless not soluble in aqueous solutions. Generally, hydrogels are crosslinked to prevent them from being soluble. Embolism protection devices comprising a swelling polymer, such as hydrogels and/or shape memory fibers, are described further in copending U.S. patent application Ser. No. 10/414,909 to Ogle, entitled "Embolism Protection Devices," incorporated herein by reference. This pending application also describes the delivery of a bioactive agent in conjunction with the embolism protection device.

With respect to the shape of the exterior of the device, this shape can be, for example, generally spherical, cylindrical, concave, or saddle shaped. A generally spherical or other shaped device may nevertheless have a roughly irregular surface contour about an average overall shape, which can orient and adjust to the vessel inside wall upon expansion. Any particular device generally can conform to the specific size and shape of the inside of the vessel following a rough size selection for the device. While the particular device size depends on the size of the particular vessel, an embolism protection device following expansion within the vessel of a human patient general can have a diameter perpendicular to the flow direction from about 50 microns to about 35 millimeters (mm), in additional embodiments from about 100 microns to about 9 mm and in further embodiments, from about 500 microns to about 7 mm. A person of ordinary skill in the art will recognize that additional ranges of device diameters within the explicit ranges are contemplated and are within the present disclosure.

In the fiber-based embodiments described herein, the outer surface of the device may be only generally defined by extrapolating between neighboring fibers along the outer portions of the structure. The nature of the arrangement of the material across the device generally is formulated to be consistent with the maintenance of flow through the device while capturing emboli over an appropriate size such that they do not flow past the device. Thus, the device can comprise a single fiber that folds to form a particular structure, multiple fibers that are arranged various ways, and the structure can comprise one or more fibers combined with one or more additional materials to form the filtering portion of the embolism protection device. For example, the fibers can be organized into a bundle that is deployed within the vessel. A bundle of fibers may or may not be associated with a fabric cover that mediates the interaction of the fibers with the vessel wall. The embolism protection device can comprise a plurality of domains with one or both of the domains comprising fibers.

Surface capillary fibers (SCF) fibers are characterized by surface channels or capillaries formed within the surface of the fiber. Surface capillaries are characterized by having a portion of the capillary exposed at the surface of the fiber along the length of the fiber. The surface capillaries result in significant increase in the surface area of the fibers relative to fibers with a smooth surface and the same diameter. The surface capillaries generally run along the length of the fiber. In some embodiments, the surface of the fiber has a plurality of surface channels or capillaries along the length of the fiber. An SCF fiber can have surface channels that essentially make up a large fraction of the bulk of the fiber such that little if any of the interior mass of the fiber is not associated with walls of one or more surface capillaries. In particular, the SCF fiber substrate can be formed with a relatively complex cross-sectional geometry. Suitable fibers include commercially available 4DG™ fibers (Fiber Innovation Technology, Inc., Johnson City, Tenn.) but would also include new advanced geometries to provide for greater fluid transport or absorption or wetting capabilities. Suitable approaches for the manufacture of the SCF are described in, for example, U.S. Pat. No. 5,200,248 to Thompson et al., entitled "Open Capillary Structures, Improved Process For Making Channel Structures And Extrusion Die For Use Therein," incorporated herein by reference. Embolism protection devices formed from fibers, such as surface capillary fibers, are described further in copending U.S. patent application Ser. No. 10/795,131 to Ogle et al., entitled "Fiber Based Embolism Protection Device," incorporated herein by reference.

For any of the embolism protection device embodiments, once the embolism protection device is positioned within a vessel, appropriate flow should be maintained through the device while emboli are trapped. Thus, with respect to the flow direction, the device has controlled porosity. This controlled porosity can be established by the nature of the material and/or by the particular structure. Specifically, the fiber density and fiber structure within the device can lead to an effective distribution of pores such that desired flow is provided while emboli are trapped. In particular, SCF fibers can trap smaller emboli within the surface capillaries, while larger emboli can be trapped along the surface and/or between fibers within the overall embolism protection device structure. In general, the desired filtering properties and corresponding average pore sizes and pore size distributions of an embolism protection device may depend on the particular location of the particular vessel in which it is delivered. However, for many applications it can be desirable to block the flow of a substantial majority of particulates with a diameter of at least about 0.2 min while allowing the flow of a substantial majority of particulates with a diameter of no more than about 0.001 mm, and in other embodiments, to block the flow of a substantial majority of particulates with a diameter of at least about 0.1 mm while allowing the flow of a substantial majority of particulates with a diameter of no more than about 0.01 mm. A person of ordinary skill in the art will recognize that additional ranges of filtering ability within the explicit ranges are contemplated and are within the present disclosure. A substantial majority of particulates can be considered to be at least about 99 percent.

An embolism protection device can comprise an attachment structure to facilitate removal of the device after sufficient time to protect against emboli. Referring to FIG. 5, embolism protection device 200 comprises two strings 202, 204 that tether device 200, although a single string or greater than two strings can be used. Device 200 is shown in an unexpanded configuration in the left side view of FIG. 5 within a catheter or hypo tube 206 and in its expanded form in the right side view of FIG. 5. By providing two strings, pulling on the strings tends to draw the strings together to contract the device if the strings are in a spaced apart attachment on the device. As shown in FIG. 6, tension on strings 202, 204, as indicated by arrow 208, is resulting in contraction in diameter of device 200 and corresponding movement from right to left, which can draw device 200 within an aspiration catheter 210. Other configurations of strings can be used to tether an embolism protection device to facilitate removal and to contract the device, which may depend on the particular shape and structure of the device. Other embolism protection device configurations that can be adapted for fiber based devices are described in copending U.S. patent application Ser. No. 10/414,909 to Ogle, entitled "Embolism Protection Devices," incorporated herein by reference.

As noted above, the embolism protection device can be part of an integrated system to provide for the delivery and/or recovery of the device. In particular, the devices are suitable for placement past an obstruction such that the embolism protection device can be deployed prior to the performance of a procedure on the obstruction. In some embodiments, the integrated apparatus generally comprises a corewire, a hypotube and the embolism protection device. Relative longitudinal motion of the hypotube over the corewire can be used to deploy the embolism protection device. In some embodiments, the hypotube is dimensioned for the placement of a treatment structure over the hypotube for treatment of an obstruction.

In some particular embodiments, the corewire has a length such that the corewire extends past the distal end of the hypotube while extending also from the proximal end of the hypotube. Generally, the corewire extends from the proximal end of the hypotube to provide for independent manipulation of the corewire relative to the hypotube, especially for longitudinal movement and from the distal end for attachment to a medical device such as an embolism protection device. In general, it is desirable to be able to transfer torque from the hypotube to the corewire to be able to rotate the tip of the corewire with less fade of the rotational motion from the proximal end to the distal end of the corewire. To accomplish this objective, it is possible to rotationally couple the hypotube without prohibiting the longitudinal motion of the hypotube relative to the corewire. For example, the coupling can be accomplished with a key/keyway interaction, a coil that couples with the application of torque or a compression coupling. The torque coupling of the hypotube and the corewire is described further in copending U.S. patent application Ser. No. 10/979,439 to Galdonik et al., entitled "Steerable Device Having a Corewire Within a Tube And Combination With a Functional Medical Component," incorporated herein by reference.

Figure 7:
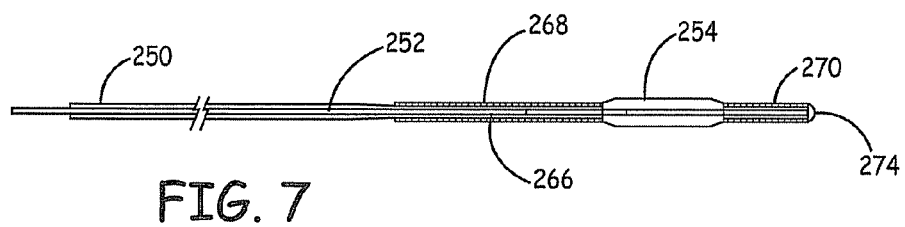
FIG. 7 is a sectional side view of a particular embodiment of an integrated guide device with an integrated embolism protection device.
Figure 8:
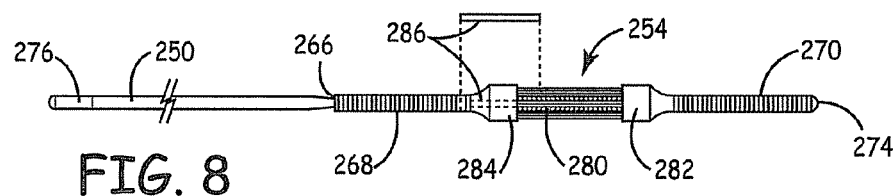
FIG. 8 is a side view of the integrated device of FIG. 7.
Figure 9:
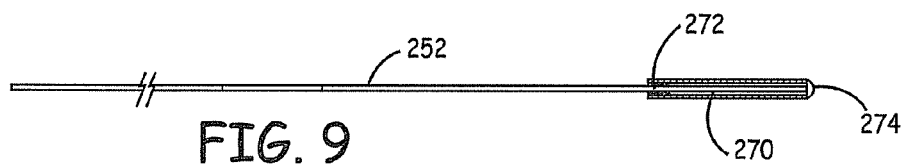
FIG. 9 is a side view of the corewire of the integrated device of FIG. 7.

One specific embodiment is shown in FIGS. 7-10. In this embodiment, the integrated instrument comprises a hypotube 250, a guidewire 252, and an embolism protection device 254. Referring to the sectional view in FIG. 7 and the side view in FIG. 8, hypotube 250 has a tapered section 266 at its distal end that mimics a taper on a conventional guidewire. A wire coil 268 is attached at the distal end of the tapered section 266 with a weld, as shown in FIGS. 7 and 8. Two layers of heatshrink polymer are applied over the coil and over at least a portion of tapered section 266. Guidewire 252 is covered with a coil 270 at its distal end, as shown in FIG. 9. Coil 270 is connected with solder 272 and a weld 274, although other attachment approaches can be used. Hypotube 250, guidewire 252, wire coil 268, coil 270 and grip 276 can all be formed from stainless steel, although other suitable materials can be used.

Figure 10:
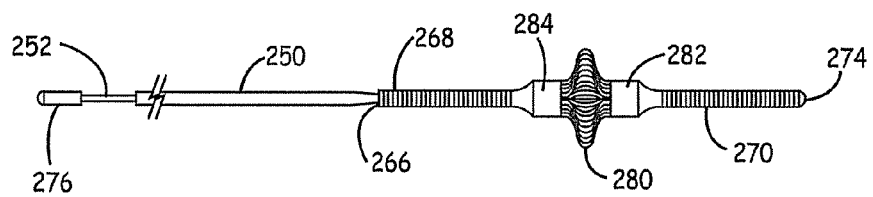
FIG. 10 is a side view of the device of FIG. 7 following expansion of the embolism protection device.

In this embodiment, embolism protection device 254 comprises a bundle of SCF fibers 280 attached at first attachment 282 and second attachment 284, as shown in FIGS. 8 and 10. A 0.1 inch long tube 436, which can be formed from polyimide polymer, is located within the second attachment 284 with guidewire 252 extending within the tube. The fibers are swaged/crimped at the two attachments 282, 284 to a diameter of 0.033 inches with radiopaque bands. After crimping, the fiber bundles are bonded at each end with an adhesive, such as cyanoacrylate, or thermally bonded.

The number of fibers in the bundle generally depends on the desired degree of filtration as well as the thickness of the fibers. In general, the number of fibers can be range from at least 10 fibers, in further embodiments from 25 fibers to 1,000,000 fibers, in other embodiments from 50 fibers to 10,000 fibers and in additional embodiments, from 100 fibers to 5,000 fibers. The length of the fibers can be selected based on the size of the corresponding vessel. When deployed, the centers of the fibers are projected across the lumen of the vessel. Thus, the unconstrained length of the fibers between attachment structures 286, 288 should be at least double the radius of the vessel. In some embodiments relating to the use of a plurality of fibers to expand within the lumen of a patient's vessel, it is generally appropriate to use fibers that have a length from about 2.2 to about 10 times the vessel radius, in some embodiments from about 2.4 to about 5 times the vessel radius and in further embodiments from about 2.6 to about 4 times the vessel radius. For placement in a human vessel, the fibers generally have a length from about 0.5 mm to about 100 mm, in other embodiments from about 1 mm to about 25 mm, and in further embodiments from about 2 mm to about 15 mm. A person of ordinary skill in the art will recognize that additional ranges of fiber numbers and fiber length within the explicit ranges are contemplated and are within the present disclosure. In one specific embodiment, the device comprises 480 in number of 6 denier SCF fibers in a bundle and a crossing profile of 0.033 inches (2.5 French).

Aspiration Catheter Materials and Improved Tracking Features

Improved tracking for aspiration catheters during delivery into a patient's vessel can be achieved through selection of materials to provide a more flexible structure at or near the distal end of the catheter, or alternatively or additionally through selection of an improved design of the catheter tip or of structures associated with the catheter tip. In general, a more flexible tip more faithfully tracks along a guide structure and more easily deflects rather than snagging on structure within a vessel. Improved tip designs can be based on a curving of the tip that provides for improved tracking especially at bends or braches in the vessel as well as a reduced likelihood of getting snagged. Similarly, in some embodiments, the tip of the catheter is constrained with respect to the position of the distal opening of the catheter with respect to the guide structure such that the tip more closely follows the guide structures while being delivered along the guide structure. While these structures may also provide somewhat of a bumper structure projecting forward from the tip, other structures have specific bumper structures projecting from the tip to resist snagging of the tip. Some of these features can be combined as appropriate. Several specific embodiments of these structures are described in detail in the following. While specific embodiments are generally discussed in the context of rapid exchange configurations, corresponding "over-the-wire" configurations can be similarly formed based on the disclosure herein.

In general, the aspiration catheter can be formed from one or more biocompatible materials, including, for example, metals, such as stainless steel or alloys, e.g., Nitinol®, or polymers such as polyether-amide block co-polymer (PE-BAX®), nylon (polyamides), polyolefins, polytetrafluoroethylene, polyesters, polyurethanes, polycarbonates or other suitable biocompatible polymers. Radio-opacity can be achieved with the addition of markers, such as platinum-iridium or platinum-tungsten or through radio-pacifiers, such as barium sulfate, bismuth trioxide, bismuth subcarbonate, powdered tungsten, powdered tantalum or the like, added to the polymer resin. Generally, different sections of aspiration catheter can be formed from different materials from other sections, and sections of the aspiration catheter can comprise a plurality of materials at different locations and/or at a particular location. For example, fittings, such as for connecting a syringe or other suction device, can be formed from a suitable material, such as one or more metals and/or one or more polymers. With respect to the catheter body, it may be desirable to form a distal section or a portion thereof of the catheter from an elastomeric polymer, such as suitable polyurethanes, polydimethyl siloxane and polytetrafluoro-ethylene. In addition, selected sections of the catheter can be formed with materials to introduce desired stiffness/flexibility for the particular section of the catheter. For example, it may be desirable to have a flexible portion at or near the distal end of the catheter. In some embodiments, a suitably flexible portion can have a material with a Shore Durometer D value of no more than 50 to achieve desired tracking properties for placement of the catheter. In some embodiments, the distal 1.5 to 2.5 centimeters have a Shore Durometer D value of about 35D, while the remaining portions of the catheter have a Shore Durometer D value of about 80D. While Shore Durometer values directly relate to hardness of the polymer, they correlate generally with flexibility and provide a convenient estimate of flexibility.

One material of particular interest is a themoplastic polymer with embedded metal wire. Suitable polymers include, for example, polyamides, i.e., nylons. The wire can be braided, coiled or otherwise placed over a polymer tubing liner with some tension. A polymer jacket is then placed over the top. Upon heating over the softening temperature of the polymer and subsequent cooling, the wire becomes embedded within the polymer. The liner and jacket can be the same or different materials. Suitable wire includes, for example, flat stainless steel wire. Some specific examples are described below. The wire adds additional mechanical strength while maintaining appropriate amounts of flexibility.

An embodiment of an aspiration catheter with improved tracking due to a curved tip is shown in FIG. 11. Aspiration catheter 300 comprises a proximal section 302, a shaft 304, a rapid exchange segment 306 and a guide port 308 at the interface of the shaft and the rapid exchange segment. Rapid exchange segment 306 has a curved tip 310. In general, a range of curved tip configurations can be suitable. The angle of the curved tip relative to a straight tip generally is less than 90 degrees and can be, for example, from about 10 degrees to about 60 degrees. The selected angle corresponds with a radius of curvature. In some embodiments, the straight portion of the tip after the curve can have a length less than about 1 cm, and in other embodiments from about 0.1 mm to about 6 mm and in further embodiments from about 0.5 mm to about 4 mm. In other embodiments, the curve consists of a gradual arc with no straight section distal to it. A person of ordinary skill in the art will recognize that additional ranges of angles and lengths within the explicit ranges above are contemplated and are within the present disclosure.

The curved tip can be formed using any suitable approach, such as molding the curved tip in the desired configuration or heating the material on a curved mandrel or in a curved trough to a softening temperature and then cooling the material on the mandrel/in the trough to fix the shape. Edge 312 of curved tip at the opening of the catheter can be cut straight perpendicular to the axis of the tip at the opening or at an angle relative to a straight cut. In some embodiments, edge 312 can have a non-planar contour.

During the delivery of catheter 300 over a guide structure, the guide structure generally extends through port 308 and out the opening of the catheter at edge 312. When aspiration catheter 300 is being advanced along a guide structure, the guide structure generally has a position extending through the patient's vessels that follows various curves and/or branches. The guide structure extending from the curved tip introduces tension on the curved tip that tends to counter elastic forces in the curved tip to followed the natural curved configuration. Generally, the curved tip is distorted by the guide structure if the tension in the guide structure exceeds the tension in the tip. This tension in curved tip 310 on the guide structure 314 tends to force the tip into a particular configuration as shown schematically in FIG. 12. In this configuration, the tip opening presents a small profile for snagging and tracks closely along the path of the guide structure as it is pushed along the guide structure. Also, the curved tip deflects the sharp edge of the tip away from the vessel wall and naturally tracks along the guide structure with little drifting since the curve creates a tight transition from the wire to the catheter on one side of the curve.

A particular embodiment with a curved tip is shown in more detail in FIGS. 13A and 13B. Catheter 320 is designed for delivery into coronary arteries, although adjustments in the sizing and configuration can be made by a person of ordinary skill in the art for use in other locations in a patient based on this design. Catheter 320 has four segments, female Luer connection 322, first shaft segment 324, second shaft segment 326 and rapid exchange segment 328. The overall length of catheter 320 is about 150 centimeters (cm).

Female Leur connector 322 generally is a molded hub formed from a suitable material, such as polycarbonate, that can be joined to first shaft segment 324. In this embodiment, first shaft segment 324 can be formed from nylon, such as nylon 11, with an embedded stainless steel braided flat wire with dimensions 0.001 inches by 0.002 inches. First shaft segment 324 has a length of about 120 cm. Two platinum-iridium radiopaque marker bands 340, 342 are placed about 45 cm and 55 cm, respectively, from the proximal end, i.e., the Leur connector end, of the catheter.

Second shaft segment 326 can be formed from a nylon polymer without metal reinforcement. Suitable nylons are commercially available from various suppliers with good resistance to stress cracking and good tensile and flexural strength. Second shaft segment 326 can have a length of 24.5 cm. Both first shaft segment 324 and second shaft segment 326 can have an outer diameter of about 0.053 inches, although other sizes can be selected for particular applications. The size can be selected to provide an inner diameter suitable for a desired amount of suction. Second shaft segment 326 provides added flexibility toward the distal end of the catheter.

Rapid exchange segment 328 has a total length of about 7.5 cm. Rapid exchange segment 328 can be formed from a nylon polymer with a stainless steel coil or braid embedded in the polymer. A suitable stainless steel has a coiled length of 6 cm, a pitch of 0.010 inches and flat wire dimensions of 0.001 inches by 0.005 inches. FIG. 13B shows an expanded view of rapid exchange segment 328 and its connection with second shaft segment 326. Port 344 is formed at the connection between rapid exchange segment 328 and second shaft segment 326. Port 344 has a diameter of about 0.0145 inches. Platinum-iridium radiopaque marker band 346 is located near the tip of rapid exchange segment 328. Opening 348 is cut at an angle from the perpendicular relative to the central axis of the lumen with the inner curve about 0.030 inches shorter than the outer curve.

Figure 14A:
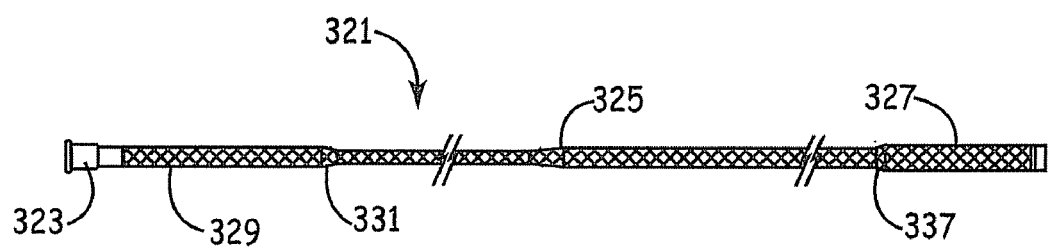
FIG. 14A is a top view of an alternative specific embodiment of a rapid exchange catheter with a curved tip, which is not visible in the top view.
Figure 14B:
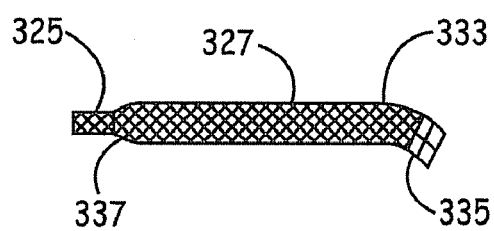
FIG. 14B is an expanded fragmentary side view of the rapid exchange tip section of the catheter of FIG. 14A.
Figure 14C:
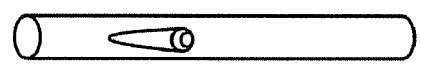
FIG. 14C is an expanded fragmentary bottom view of the guide port of the aspiration catheter of FIG. 14A.

A similar embodiment is shown in FIG. 14A. Referring to FIG. 14A, aspiration catheter 321 comprises a female Leur lock connector 323, shaft 325, and rapid exchange segment 327. Shaft 325 has braided wire along its entire length. Two colored bands 329, 331 are located along shaft 325 to provide information on the position of the catheter to the operator. Rapid exchange segment 327 also has braided wire which can cover its entire length or there can be a small gap of a few millimeters or less adjacent shaft 325. In some embodiments, rapid exchange segment 327 has an approximately equal or just slightly smaller diameter as shaft 325. Rapid exchange segment 327 has a curved tip 333 as shown in FIG. 14B. The distal 1.5 centimeters of the tip, including the curve, are made form a particularly soft material. A radiopaque marker 335 can be placed near the tip. Referring to FIG. 14C, for embodiments in which the differences in diameter of shaft 325 and rapid exchange segment 327 are small, guide port 337 can be formed by deforming a trough 339 into the distal edge of the shaft where it meets the rapid exchange segment. For use in different sized blood vessels, the outer diameter of the shaft may range form about 0.05 inches to about 0.07 inches and the thickness can be roughly 0.01 inches. The rapid exchange segment may have a similar outer diameter as the shaft or an outer diameter larger than the shaft outer diameter by about 0.02 inches or less.

Some embodiments have structure that constrains the relationship of the guide structure to the tip opening while the catheter is being positioned but releases the guide structure if an embolism protection device is drawn into the opening. The tip portion 360 of such a structure is shown in FIG. 15. Tip portion 360 can be a portion of a rapid exchange segment or the distal section of an over-the-wire aspiration catheter. Tip portion 360 comprises an aspiration opening 362 and an extension 364 with a guide lumen 366. Guide lumen generally has an inner diameter just larger than the guide structure to facilitate controlled tracking. Extension 364 is operably connected with the edge of aspiration opening 362. Extension 364 has a slit 368. As shown in FIG. 15, a guide structure 370 extends from opening 362 through guide lumen 366 and projects forward. Guide structure 370 comprises an embolism protection device 372. Due to slit 368, extension 364 opens along the slit if the wider embolism protection device is drawn toward opening 362. As embolism protection device 372 passes past extension 364 toward opening 362, extension 364 releases guide structure 370, and embolism protection device 372 can be brought into opening 362.

A specific embodiment similar to the embodiment of FIG. 15 is shown in detail in FIGS. 16 and 17. Catheter 380 has five segments, connector 382, first shaft segment 384, second shaft segment 386, rapid exchange segment 388 and extension 390. The total length without the tip extension is about 150 cm. Connector 382 can be a female Leur lock connector formed from clear polycarbonate. First shaft segment 384 and second shaft segment 386 are equivalent, respectively, to first shaft segment 324 and second shaft segment 326 described above with respect to FIG. 13A. Rapid exchange segment 388 is comparable to the rapid exchange segment 328 of FIGS. 13A and 13B except that rapid exchange segment 388 is straight and not curved. Rapid exchange segment 328 has a length of about 5.5 cm. Rapid exchange segment 388 has a slanted opening 392 connected adjacent its longest edge to extension 390. Extension 390 can be formed from the same polymer as rapid exchange segment 388.

FIG. 17 has an expanded view of rapid exchange segment 388, the adjacent portion of second shaft segment 386 and extension 390. Port 394 is formed at the interface between second shaft portion 386 and rapid exchange segment 388. Port 394 provides for a guide structure to extend through the rapid exchange segment 386 without extending through the shaft segments. A slit 396 along extension 390 can be seen in a perspective view in the insert of FIG. 17.

Figure 18:
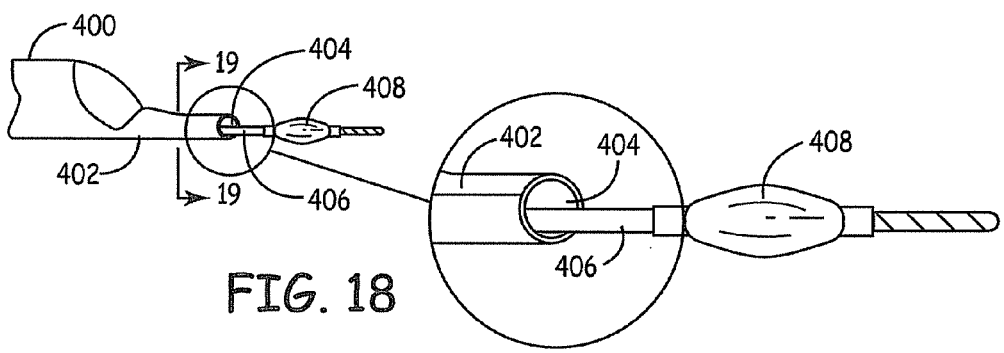
FIG. 18 is a fragmentary side perspective view of an alternative embodiment of an aspiration catheter having an extension at its tip with a guide lumen with an insert depicting an expanded alternative perspective view of the extension.
Figure 19:
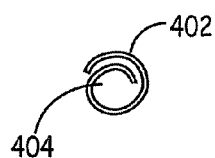
FIG. 19 is a sectional view of the extension of FIG. 18 taken along line 19-19 of FIG. 18.
Figure 20:
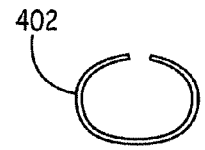
FIG. 20 is a sectional side view of the extension of FIG. 18 in a configuration in which the extension has opened along folds.

An embodiment is shown in FIG. 18 similar to the embodiments shown in FIGS. 15-17. Catheter tip 400 in FIG. 18 has an extension 402 with an overlapping polymer coil having a guide lumen 404. A guide structure 406 with an embolism protection device 408 is shown extending through guide lumen 404. The insert in FIG. 18 shows an expanded alternative perspective view of the extension 402. A sectional view is shown in FIG. 19. The overlapping polymer coil can expand, as shown in a sectional view of FIG. 20, in response to forces, for example, from embolism protection device 408 being drawn toward catheter tip 400 such that a gap opens with the coil no longer overlapping. A guide structure can be released through the gap.

Six representative embodiments are presented that provide a deflection structure with a bumper at the catheter tip that inhibits snagging of the catheter opening and/or limits the movement of the tip relative to the guide structure to promote more true tracking as the aspiration catheter is being advanced. In appropriate embodiments, the bumper structure withdraws at least partially into the aspiration lumen to provide for drawing an embolism protection device into the catheter, while in other embodiments, the deflection structure can be completely removed from the aspiration catheter. The alternative embodiments with deflection structures can be based on the same basic catheter structure with different deflection structures associated with the aspiration catheter. A representative basic catheter structure is described in detail with respect to FIGS. 21 and 22 with specific deflection structures described subsequently.

Figure 21:
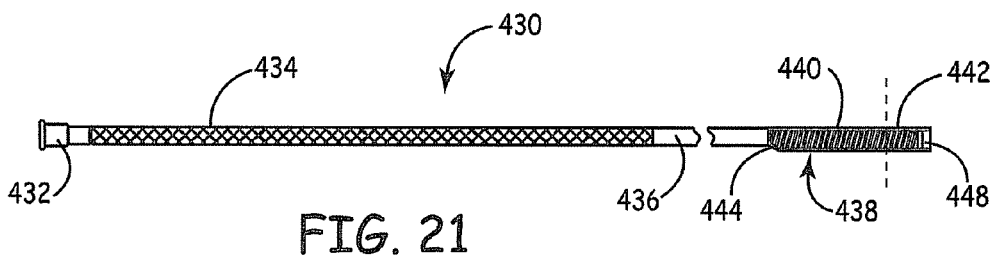
FIG. 21 is a side view of a rapid exchange aspiration catheter suitable for use with a deflection structure having a bumper.
Figure 22:
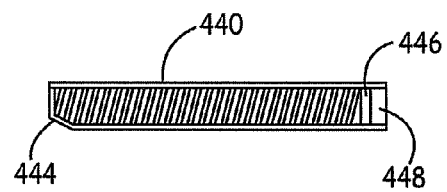
FIG. 22 is an expanded side view of a rapid exchange segment of the aspiration catheter of FIG. 21.

Referring to FIGS. 21 and 22, aspiration catheter 430 comprises a connector 432, a first shaft segment 434, a second shaft segment 436 and rapid exchange segment 438. Connector 432, e.g., a Leur lock connector, first shaft segment 434 and second shaft segment 436 can be similar to their corresponding components in FIGS. 13 and 16. In this embodiment, rapid exchange segment 438 has a length of 6.5 cm with a first portion 440 with a length of 4.5 cm formed from polyamide/nylon polymer and a second portion 442 with a length of 2 cm at the tip formed from a polyether-block-amide copolymer. A flat wire coil is embedded in the polymer of rapid exchange segment 438 as described above with respect to FIGS. 16 and 17. Port 444 is located at the interface between second shaft segment 436 and rapid exchange segment 438. A radiopaque (platinum with 10% iridium) marker band 446 is placed adjacent tip opening 448. An expanded view of rapid exchange segment 438 is shown in FIG. 22. As shown in FIGS. 21 and 22, the aspiration catheter tip is straight. However, a curved tip, such as shown in FIGS.

11-14, can be substituted for the straight tip. Most of the bumper structures shown in FIGS. 23-36 below have sufficient flexibility that they can be adapted for use with a curved tip catheter.

Figure 23:
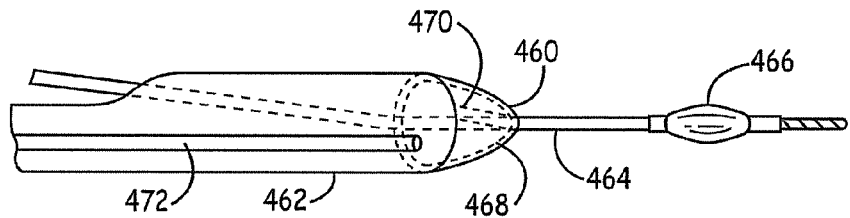
FIG. 23 is a fragmentary side perspective view of the distal end of an aspiration catheter having a first embodiment of a deflection structure having a bumper.
Figure 24:
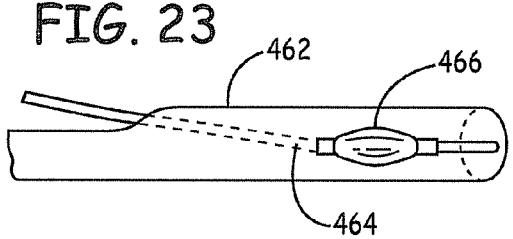
FIG. 24 is a fragmentary side perspective view of the aspiration catheter of FIG. 23 in which the bumper and an embolism protection device have been withdrawn into the aspiration catheter.
Figure 25:
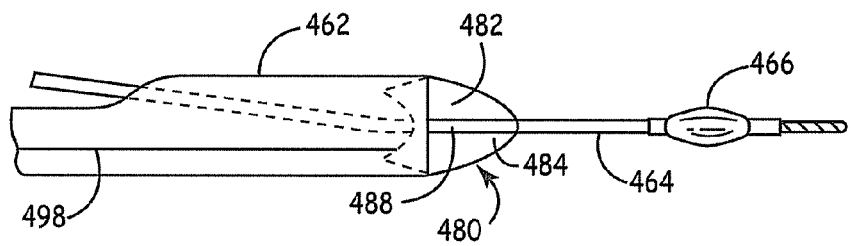
FIG. 25 is a fragmentary side perspective view of the distal end of an aspiration catheter having a second embodiment of a deflection structure having a bumper, in which hidden structure is shown with phantom lines.

A first representative embodiment of deflection structure with a bumper for the aspiration catheter tip is shown in FIGS. 23 and 24. Bumper 460 is associated with aspiration catheter 462 and guide structure 464 that has an associated embolism protection device 466. Bumper 460 has a cup shape with an opening 468 at the bottom of the cup and a slit 470 along its side. Generally, opening 468 is just slightly larger than the diameter of the guide structure. The curved sides of the cup shape provide significant function as a bumper. Bumper 460 is associated with a tether 472, which can be, for example, a thin cable or the like comprising metal, polymer, combinations thereof or the like.

In general, bumper 460 can be formed successfully from either a soft material, such as a urethane or silicone polymer, or a stiff material, such as stainless steel. Generally, the bumper sticks out from about 1 mm to about 6 mm, and in further embodiments from about 2 mm to about 4 mm. A person of ordinary skill in the art will recognize that additional ranges of extension within the explicit ranges above are contemplated and are within the present disclosure. Generally, friction holds the bumper in position while the catheter is being delivered.

For the retraction of embolism protection device 466 into the tip of aspiration catheter 462 during retrieval of the embolism protection device as well as in preparation for the application of suction, bumper 460 is removed from the catheter. Tether 472 can be used to withdraw bumper 460 through the aspiration lumen. Upon pulling bumper 460 with tether 472, slit 470 provides for bumper 460 to disassociate from guide structure 464. Bumper 460 can be somewhat elastic to facilitate its removal through the aspiration lumen. In alternatively embodiments, guide structure 464 can run along side bumper 460 rather than through an opening in the bumper such that a slit is not needed to separate the bumper from the guide structure.

Figure 26:
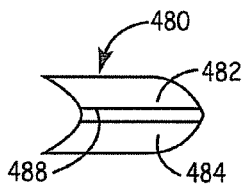
FIG. 26 is a side view of the bumper of FIG. 25.
Figure 27:
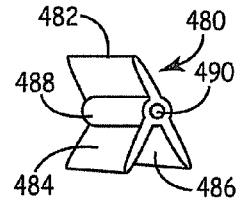
FIG. 27 is a front perspective view of the bumper of FIG. 25.
Figure 28:
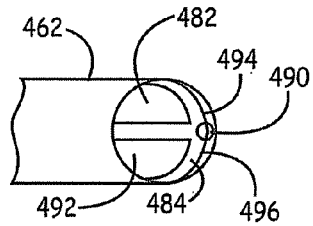
FIG. 28 is a fragmentary, front perspective view of the aspiration catheter of FIG. 25 showing the bumper extending from the catheter opening.

Another embodiment of a deflection structure is shown in FIGS. 25-29. In this embodiment, bumper 480 replaces bumper 460 of FIG. 23. Referring to FIGS. 26 and 27, bumper 460 has three arms 482, 484, 486 around a central core 488. While the bumper is shown with three arms, suitable bumpers could similarly have two arms or four or more arms. The edges of the arms have a diameter approximately corresponding with the inner diameter of the aspiration catheter at its distal end. Arms 482, 484, 486 have a curved back structure such that the convex surfaces project from the tip of aspiration catheter 462, as shown in FIG. 28. Central core 488 has a guide structure lumen 490 such that guide structure 464 can pass bumper 460 through central lumen 490. As an alternative, guide structure 464 can pass between a pair of arms as an alternative to passing through central lumen 490, which then becomes optional. When bumper 480 is positioned at the tip of catheter 462, arms 482, 484, 486 form three aspiration channels 492, 494, 496 into the catheter suction lumen, as shown in FIG. 28. Thus, suction can be effective with the use of bumper 460. Tether 498 connects bumper 460 to the exterior of the catheter and can be used to move the bumper away from the opening to the suction lumen.

Figure 29:
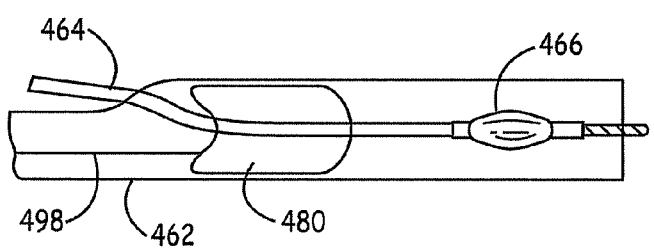
FIG. 29 is a fragmentary side cut away view of the aspiration catheter of FIG. 25 in which the bumper and an embolism protection device have been withdrawn into the aspiration catheter, in which the wall of the vessel is removed to show structure within the vessel.

Again, this bumper can be successfully formed from a soft material or a stiff material, although a soft material may be preferred for this embodiment to provide a desired degree of friction to hold the bumper in place during delivery. While bumper 460 does not block aspiration, the position of bumper 460 at the tip of aspiration catheter 462 blocks the entrance of embolism protection device 466 into aspiration catheter 462. Therefore, it is desirable to withdraw bumper 460 into the aspiration catheter lumen, as shown in FIG. 29, when recovering embolism protection device 466. The bumper can be pulled into the lumen using tether 498.

Figure 30:
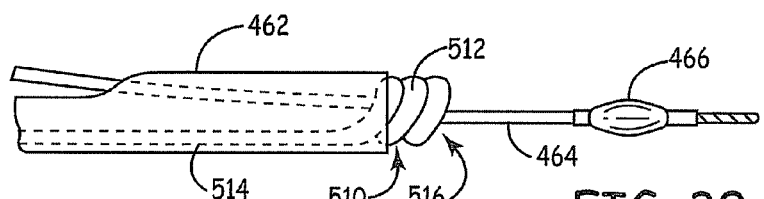
FIG. 30 is a fragmentary side view of the distal end of an aspiration catheter having a third embodiment of a deflection structure having a bumper, in which hidden structure is shown with phantom lines.
Figure 31:
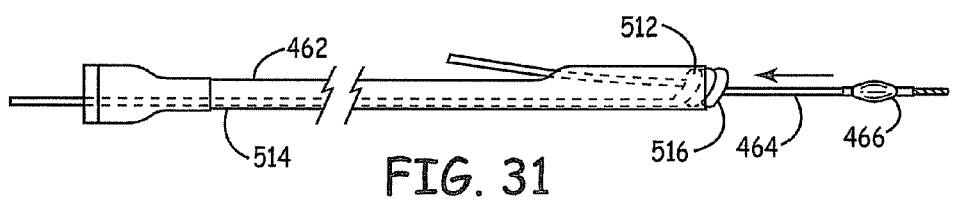
FIG. 31 is a fragmentary side view of the aspiration catheter of FIG. 30 in which the bumper has been partially withdrawn into the aspiration catheter.
Figure 32:
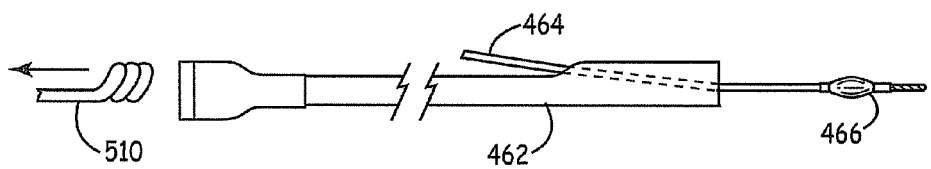
FIG. 32 is a fragmentary side view of the aspiration catheter of FIG. 30 in which the bumper has been withdrawn from the aspiration catheter.

A third embodiment of a deflection structure is shown in FIGS. 30-32. In this embodiment, deflection structure 510 comprises a coil 512 and a shaft 514. The coil forms a central channel 516 such that guide structure 464 traverses the central channel 516. During delivery, coil 512 extends from the tip of aspiration catheter 462, as shown in FIG. 30. Thus, coil 512 functions as a bumper. Central channel 516 also constrains the movement of the tip of aspiration catheter 462 relative to guide structure 464 such that the aspiration catheter tracks more faithfully along the guide structure. However, coil 512 does not provide a sufficient aspiration lumen. Therefore, once aspiration lumen 462 is in position or nearly so, it is desirable to remove deflection structure 510 from aspiration catheter 462.

Coil 512 can be formed, for example, from polymer or stainless steel. Metal can provide desirable levels of tensile strength. Referring to FIG. 31, deflection structure 510 can be pulled back toward the proximal end of aspiration catheter 462 using shaft 514. Coil 512 releases from guide structure 464 when the coil is pulled since the coil unravels. As shown in FIG. 32, coil 512 can be completely removed from aspiration catheter prior to application of suction and retrieval of embolism protection device 466.

Figure 33:
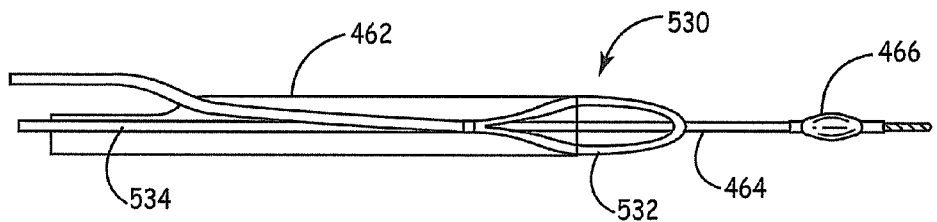
FIG. 33 is a fragmentary side view of an aspiration catheter having a fourth embodiment of a deflection structure having a bumper.
Figure 34:
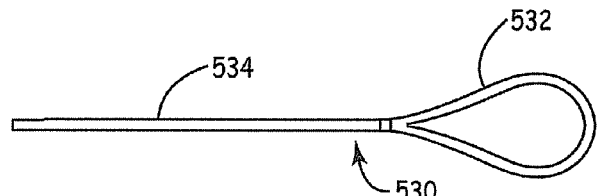
FIG. 34 is a fragmentary side view of the deflection structure of FIG. 33.

A fourth embodiment of a deflection structure is shown in FIGS. 33 and 34. In this embodiment, deflection structure 530 comprises an elastic loop 532 and a tether 534. Elastic loop 532 tends to keep its natural shape shown in FIG. 34. During deployment of aspiration catheter 462, elastic loop 534 extends from the tip of the catheter as shown in FIG. 33 and is under tension due to compression to fit within the aspiration catheter. Tension in loop 534 tends to hold deflection structure 530 in place during the delivery of aspiration catheter 462. Loop 534 can be formed, for example, from a spring metal, such as Elgiloy®, a cobalt-chromium-nickel alloy or MP35N, a nickel-cobalt-chromium-molybdenum alloy. Tether 534 can be formed from any reasonable biocompatible material.

While deflection structure 530 generally may not interfere significant with suction, deflection structure 530 can interfere with drawing embolism protection device 466 into aspiration catheter 462. Therefore, once aspiration catheter 462 is in position, loop 534 can be withdrawn partially within or completely from the aspiration catheter to leave the tip of the catheter unobstructed. Loop 534 can be moved relative to aspiration catheter 462 by pulling on tether 534.

A fifth embodiment of a deflection structure is shown in FIG. 35. In this embodiment, deflection structure 540 has a prolapsed deflection tip 542 extending from a tether 544. Prolapsed deflection tip 542 is similar to loop 532 in the embodiment in FIGS. 33 and 34. During delivery of aspiration catheter 462, the bend of prolapsed deflection tip 542 extends from the tip of the catheter to function as a bumper. Prolapsed deflection tip 542 may or may not be resilient. Prolapsed deflection tip 542 can be withdrawn partially within or fully from aspiration catheter 462 by pulling on tether 544 to remove obstruction of the catheter opening such that embolism protection device 466 can be withdrawn into the aspiration catheter. Deflection tip 542 and tether 544 may or may not be formed from the same material, such as suitable biocompatible metal(s) and/or polymer(s).

A sixth embodiment of a deflection structure is shown in FIG. 36. In this embodiment, deflection structure 550 comprises a rod 552 with a deflection tip 554. The diameter of rod 552 and/or deflection tip 554 can be selected to introduce the desired bumper effect from the tip. During delivery of aspiration catheter 462 over guide structure 464, deflection tip 554 extends from the opening at the tip of the catheter. Deflection structure 550 can be withdrawn when aspiration catheter 462 is in position such that suction can be applied, and/or embolism protection device 466 can be withdrawn into the aspiration catheter. Movement of deflection structure 550 relative to aspiration catheter 462 can be accomplished by pulling on rod 552. Deflection structure 550 can be formed from any suitably flexible biocompatible material, such as suitable metal(s) and/or polymer(s).

Methods for Using Aspiration Catheters and Retrieving Embolism Protection Devices Use of Aspiration Catheter and Removal of Embolism Protection Devices In general, the aspiration catheters described herein can be used for a variety of procedures. Specifically, the improved aspiration catheters can be used generally for any procedures that use an aspiration catheter to take advantages of the improved delivery of the catheter. However, the aspiration catheters are particularly useful for the removal of an embolism protection device from the vessel of a patient. In particular, the aspiration can be effective to capture emboli that may be released while the embolism protection device is being converted from a deployed orientation to an appropriate orientation for removal. To stabilize the recovery process, the embolism protection device can be drawn into a sheath, generally the distal end of the aspiration catheter. Once the embolism protection device is safely within the aspiration catheter, the risk of release of emboli is sufficiently reduced that the suction can be stopped and the embolism protection device safely withdrawn from the patient along with the aspiration catheter. In some embodiments, aspiration can be applied during a portion of the period in which the aspiration catheter is being put into position while the embolism protection device is deployed in a filtering configuration. Thus, by drawing the embolism protection device into a distal end of the catheter, the disruption of flow from the suction can be kept to a level such that a shunt for the flow may not be used. Radiopaque markers on the medical devices can be used for positioning during the various steps of the process.

Many of improved designs described above provide for improved tracking of the catheter over a guide structure during deployment. Many of the designs have tighter tracking along the guide structure and/or at least partial occlusion of a distal port to reduce the chances of snagging of the catheter during delivery. If there is snagging during delivery, the catheter can be gently pulled back, turned, for example, a quarter turn, and advanced again. In general, this approach can be successful for the delivery of the catheter into even very difficult to reach vessels. Once the catheter is at a desired position, any obstructions to the distal opening of the catheter can be withdrawn into the lumen at a parked position, if the structure does not significantly obstruct suction, or can be removed from the catheter. With the distal opening clear, an embolism protection device can be withdrawn into the tip of the catheter. To do this, generally the catheter is left stationary and the device is pulled into the catheter, although in principle the catheter can be moved in the process as an alternative or in addition to moving the device.

In general, it is desirable to keep the time for the application of suction to lower values to avoid undesirable disruption of the flow through the vessels. Using the improved embolism protection devices described herein and in copending applications cited herein, procedures can be safely performed without blocking the flow through the patient's vessel. Similarly, the use of an embolism protection device with a three dimensional matrix provides for removal of the device into the aspiration catheter without blocking suction into the catheter through flow through the matrix and/or by having a recovery configuration that does not block flow, although a side port in the aspiration catheter can complement aspiration through the distal tip of the catheter. Depending on the vessel, the amount of disruption of the flow that can be safely tolerated can be estimated, such that the process for the recovery of the embolism protection device can be accordingly determined.

To keep disruption of the flow to lesser levels, the suction generally is applied starting shortly before the recovery process begins. However, in some embodiments suction can be applied while the aspiration catheter is being put into position while the embolism protection device is deployed in a filtering configuration. Suction can be applied once the aspiration catheter clears the introducer catheter until the aspiration catheter is near the filter or for some fraction of this time. In some embodiments, one or two syringes can be withdrawn during the positioning of the aspiration catheter for recovery of a filter. Suction generally can be maintained during the constriction of the device configuration for fitting within the opening of the aspiration catheter and while the device is drawn within the catheter. The suction generally is stopped once the device is within the aspiration catheter, and the device generally is not moved further relative to the aspiration catheter.

To draw the embolism protection device within the aspiration catheter, the embolism protection device can be converted from a deployed configuration across the vessel lumen to a recovery configuration, generally with a reduced area across the cross section of the vessel lumen, in which the device fits within the aspiration catheter. By directly converting the embolism protection device to a recovery configuration, the embolism protection device can be formed without structural elements, such as metal struts, to facilitate the mechanical collapse of the device through pressure against the catheter end. This change of configuration can be accomplished with an actuation element that directly converts the device between different configurations. The recovery configuration may or may not be similar to the delivery configuration. In some embodiments, an actuation element transforms the embolism protection device between delivery configuration to a deployed configuration and subsequently from a deployed configuration to a recovery configuration. In other embodiments, some type of gripping or engaging tool can be used to mechanically compress the embolism protection device to a recovery configuration. In additional embodiments, the process of drawing of the embolism protection device into the distal compartment can compress the embolism protection device into the recovery configuration. To facilitate this mechanical compression, the end of the distal compartment can be tapered and/or the proximal end of the embolism protection device can be tapered to facilitate the entrance of the initial portion of the device into the compartment. Thus, the transformation into the recovery configuration and the loading of the device into the distal compartment can be simultaneous steps or sequential steps.

As described above, components used to improve tracking and/or reduce snagging of the aspiration catheter during delivery may need to be removed or withdrawn into the aspiration catheter to provide a sufficient aspiration lumen and/or to avoid blockage of entry of an embolism protection device into the aspiration catheter. Specifically, the aspiration catheter embodiments in FIGS. 23-36 involve some reconfiguration or removal of a bumper structure to provide for entry of an embolism protection device into the end of the aspiration catheter. Generally, this reconfiguration and/or removal of the bumper is performed prior to application of suction and generally also before reconfiguration of the embolism protection device to a recovery configuration.

The overall timing of the recovery process involves a balance between several factors within the overall objective of keeping the period of application of suction within desired ranges. To meet the objectives, it is desirable to transform the embolism protection device to the recovery configuration and load the embolism protection device into the aspiration catheter relatively quickly. In general, it is desirable for the total time to transform the device to the recovery configuration and to load the device within the distal compartment to be no more than about five minutes, in other embodiments, no more than about 3 minutes, in additional embodiments from about 2 seconds to about 2 minutes and in further embodiments from about 5 seconds to about 1.5 minutes. Generally, the suction is not applied for more than about 10 seconds, in some embodiments no more than about 5 seconds and in further embodiments no more than about 2 seconds prior to commencing the transformation of the device to the recovery configuration. Similarly, the suction generally is applied for no more than about 10 second, in some embodiments no more than about 5 seconds and in further embodiment no more than about 2 seconds after the embolism protection device is loaded into the distal compartment. A person of ordinary skill in the art will recognize that additional ranges of times within the explicit ranges above are contemplated and are within the present disclosure.

The suction is contrary to the flow within the vessel, which is otherwise relatively unrestricted. The suction rate can be greater than the flow within the vessel or some fraction of the flow. If the suction rate is greater than the natural flow rate, the suction tends to draw fluid from both sides of the embolism protection device into the aspiration catheter. If the suction rate is less than the natural flow rate, the suction tends to draw fluid from the portion of the vessel adjacent the opening of the aspiration catheter. The suction rate can be selected to balance the disruption of the flow with the collection rate for any released emboli. In some embodiments, the flow rate can change at different points in the recovery process. For variable suction rate embodiments, the suction rate is generally greater at the start of the recovery process and reduced once the device is collapsed to a recovery configuration.

Based on conventional practices by physicians in the field, the use of syringes can be convenient. Desirable results have been obtained with a 30 cubic centimeter, i.e., 30 ml, syringe. The rate of filling the syringe generally depends on the diameter of the shaft of the catheter. Typical times to fill a syringe range from about 10 second to about 25 seconds with shorter times for larger diameter catheters, which are generally used in larger blood vessels. In some embodiments, a first syringe is filled during delivery of the catheter into position. A second syringe is filled while collapsing the filter and withdrawing the filter into the tip of the catheter. For the embolism protection device shown in FIGS. 7-10, physicians have successfully converted the device into a retreval configuration and withdrawn the device into the aspiration catheter in roughly 10-12 seconds under actual clinical conditions in human patients. In lab bench simulations, emboli capture efficiencies from 96 to 100% have been achieved with this procedure. In general, the time to fill the syringe is a balance of having time to collapse and retrieve the device with having a sufficient flow into the catheter to reduce the chance of emboli escape.

Figure 37:
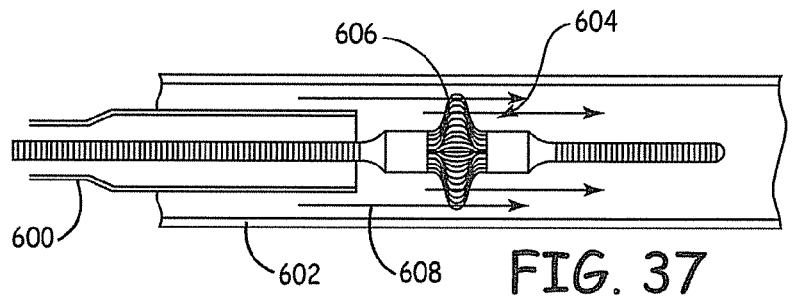
FIG. 37 is a side view of an aspiration catheter positioned within a patient's vessel adjacent a deployed embolism protection device of FIGS. 7-10.
Figure 38:
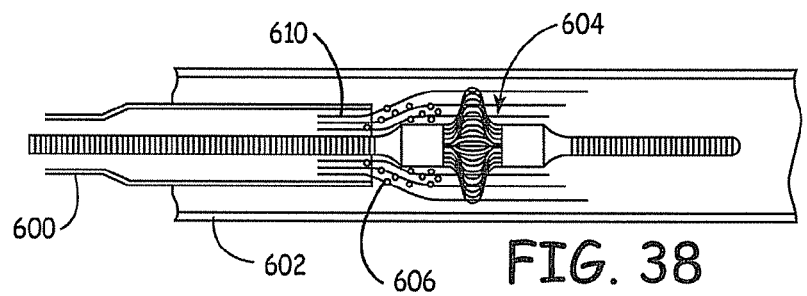
FIG. 38 is a side view of the aspiration catheter of FIG. 37 with suction being applied.
Figure 39:
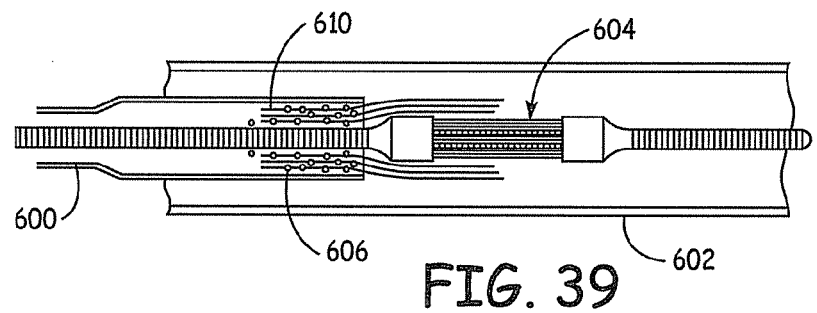
FIG. 39 is a side view of the aspiration catheter of FIG. 37 with suction being applied and with the embolism protection device converted to a recovery configuration.
Figure 40:
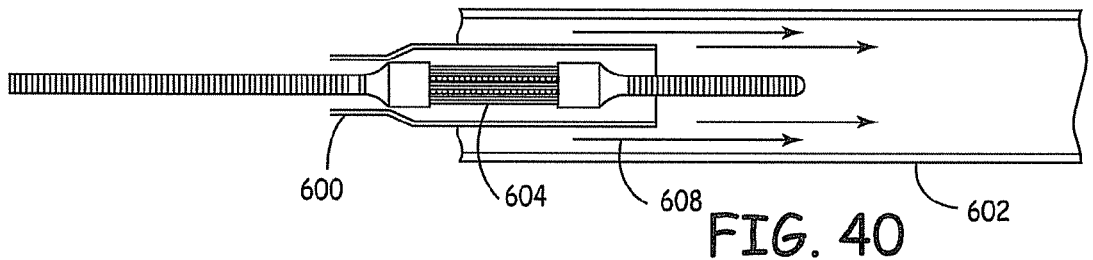
FIG. 40 is side view of the aspiration catheter of FIG. 37 with the embolism protection device within the aspiration catheter.

FIGS. 37-40 depict the generic recovery of the embolism protection device of FIGS. 7-10. FIG. 37 depicts an aspiration catheter 600 within a patient's vessel 602 a short distance downstream from embolism protection device 604. Emboli 606 are schematically depicted within device 604 and along the downstream surface of the device. Flow through the vessel is depicted with flow arrows 608. As shown in FIG. 38, suction is applied just before embolism protection device 604 is reconfigured to a recovery configuration. Flow from the suction is depicted with flow arrows 610. FIG. 39 depicts embolism protection device 604 reconfigured to a recovery configuration. Suction is still being applied. Referring to FIG. 40, embolism protection device 604 is withdrawn into aspiration catheter 600. Suction has been turned off in FIG. 40 with essentially unrestrained flow restored in vessel 602.

Packaging and Distribution

The medical devices described herein are generally packaged in sterile containers for distribution to medical professionals for use. The articles can be sterilized using various approaches, such as electron beam irradiation, gamma irradiation, ultraviolet irradiation, chemical sterilization, and/or the use of sterile manufacturing and packaging procedures. The articles can be labeled, for example with an appropriate date through which the article is expected safely to remain in fully functional condition.

Various devices described herein can be packaged together in a kit for convenience. For example, an aspiration catheter can be packaged along with an integrated system for delivery and recovery of an embolism protection device. The kit can further include, for example, labeling with instruction for use and/or warnings, such as information specified for inclusion by the Food and Drug administration. Such labeling can be on the outside of the package and/or on separate paper within the package.

The embodiments described above are intended to be illustrative and not limiting. Additional embodiments are within the claims. Although the present invention has been described with reference to preferred embodiments, workers skilled in the art will recognize that changes may be made in form and detail without departing from the spirit and scope of the invention. Any incorporation by reference of documents above is limited so that no subject matter is incorporated that is contrary to the explicit disclosure herein.

What is claimed is:
1. An aspiration catheter comprising:
a suction device,
a proximal portion, and
a shaft with a proximal end and a distal end,
wherein the shaft is operably connected at its proximal end to the proximal portion to form a suction lumen,
wherein the suction device is attached or attachable to the proximal portion to operably connect the suction device to the suction lumen,
wherein the distal end of the shaft comprises a tip portion having an aspiration opening at the distal end of the tip that is in fluid communication with the suction device through the suction lumen,
wherein the tip portion has greater flexibility relative to the rest of shaft and has a natural curve that is curved from about 10 degrees to less than 90 degrees relative to a straight orientation of the shaft,
wherein the shaft comprises a single lumen rapid exchange segment near the distal end of the shaft and a guide port adjacent the rapid exchange segment, the guide port having a suitable size for the passage of a guide structure with a configuration for the guide structure to extend through the guide port and through the aspiration opening, and wherein a longitudinal cross sectional view of the curved tip portion is characterized by a top curve and a lower curve that bend in the same direction with respect to the longitudinal axis of the catheter.

2. The aspiration catheter of claim 1 wherein the suction device comprises a syringe and wherein the proximal portion comprises a Luer lock attachable to the syringe.

3. The aspiration catheter of claim 1 wherein the suction device comprises a pump.

4. The aspiration catheter of claim 1 wherein the shaft has a length from about 50 cm to about 300 cm.

5. The aspiration catheter of claim 1 wherein the shaft has an outer diameter from about 0.010 inches to about 0.065 inches.

6. The aspiration catheter of claim 1 wherein the shaft comprises a polymer with a metal reinforcement embedded in the polymer.

7. The aspiration catheter of claim 1 wherein the shaft comprises a first segment and a second segment distal to the first segment and wherein the first segment comprises a polymer with metal reinforcement and the second segment comprises a polymer without metal reinforcement.

8. The aspiration catheter of claim 7 wherein the rapid exchange segment is operably connected to the second segment with the guide port at or near the interface of the rapid exchange segment and the second segment, the rapid exchange segment comprising polymer with metal reinforcement.

9. The aspiration catheter of claim 1 wherein the shaft comprises a polymer with embedded braided metal.

10. The aspiration catheter of claim 1 wherein the curved tip portion is from about 30 degrees to about 60 degrees relative to if the tip portion were straight.

11. The aspiration catheter of claim 1 wherein the tip portion distal to the curve is straight with the straight portion having a length less than about 4 mm.

12. The aspiration catheter of claim 1 wherein the shaft comprises side ports in fluid communication with the suction lumen.

13. The aspiration catheter of claim 1 wherein the distal end of the shaft is beveled.

14. The aspiration catheter of claim 1 wherein the shaft has an axis and wherein the distal end of the shaft is substantially perpendicular to the axis of the shaft.

15. The aspiration catheter of claim 1 wherein the catheter is used in a coronary artery.

16. The aspiration catheter of claim 1 wherein the catheter is used in a carotid artery.

17. A method for the delivery of an aspiration catheter with a distal aspiration opening into a vessel, wherein the aspiration catheter comprises a shaft comprises a proximal end, a distal end, a single lumen rapid exchange segment comprising a curved catheter tip near the distal end of the shaft, and a guide port adjacent the single lumen rapid exchange segment, the method comprising, pre-delivering a guide structure into the vessel, and tracking the single lumen rapid exchange segment of the catheter along the guide structure with the guide structure extending through the guide port and from the distal aspiration opening and the curved catheter tip being distorted from its natural curved configuration due to forces exerted between the curved catheter tip and the guide structure exiting the distal aspiration opening to deliver the catheter into the vessel, wherein the natural curve of the catheter tip is from about 10 degrees to less than 90 degrees relative to if the catheter tip is straight, wherein the shaft comprises a metal braid within a polymer to increase torque transmittal along the length of the catheter, wherein the guide port has a suitable size for the passage of the guide structure, and wherein a longitudinal cross sectional view of the natural curve of the catheter tip is characterized by a top curve and a lower curve that bend in the same direction with respect to the longitudinal axis of the catheter.

18. The method of claim 17 wherein the guide structure comprises a filter element.

\* \* \* \* \*